(12) United States Patent
Endo

(10) Patent No.: US 12,198,798 B2
(45) Date of Patent: Jan. 14, 2025

(54) MEDICAL IMAGE PROCESSING SYSTEM AND OPERATION METHOD THEREFOR

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 366 days.

(21) Appl. No.: 17/672,247

(22) Filed: Feb. 15, 2022

(65) Prior Publication Data
US 2022/0172827 A1 Jun. 2, 2022

Related U.S. Application Data

(63) Continuation of application No. PCT/JP2020/030875, filed on Aug. 14, 2020.

(30) Foreign Application Priority Data

Aug. 27, 2019 (JP) .................................. 2019-154640

(51) Int. Cl.
*G16H 30/40* (2018.01)
*G06T 7/00* (2017.01)
(Continued)

(52) U.S. Cl.
CPC .......... *G16H 30/40* (2018.01); *G06T 7/0012* (2013.01); *G06T 7/20* (2013.01); *G06V 10/25* (2022.01); *G06T 2207/10068* (2013.01)

(58) Field of Classification Search
CPC ................... G06T 7/0012; G06T 7/20; G06T 2207/10068; G06V 10/25; G06V 10/945; G06V 2201/03; G16H 50/20; A61B 1/045
See application file for complete search history.

(56) References Cited

U.S. PATENT DOCUMENTS

2012/0274754 A1  11/2012  Tsuruoka
2015/0276602 A1  10/2015  Ishihara
(Continued)

FOREIGN PATENT DOCUMENTS

JP    2011-160848 A    8/2011
JP    2014-161537 A    9/2014
(Continued)

OTHER PUBLICATIONS

"Notice of Reasons for Refusal" Office Action issued in JP 2021-542746; mailed by the Japanese Patent Office on Aug. 29, 2022.
(Continued)

*Primary Examiner* — Dhaval V Patel
(74) *Attorney, Agent, or Firm* — Studebaker & Brackett PC

(57) ABSTRACT

There are provided a medical image processing system with which a notification of detection of a region of interest can be appropriately given and an operation method therefor. A region of interest is detected from an endoscopic image captured by an endoscope. When a region of interest is detected, the endoscopic image in which the region of interest is highlighted is displayed on a display device (50) to thereby give a notification of detection of the region of interest. After notification, the degree of highlight of the region of interest is changed in accordance with the amount of movement of the endoscope estimated from the endoscopic image.

16 Claims, 21 Drawing Sheets

(51) Int. Cl.
*G06T 7/20* (2017.01)
*G06V 10/25* (2022.01)

(56) References Cited

U.S. PATENT DOCUMENTS

| | | | | |
|---|---|---|---|---|
| 2015/0363942 | A1* | 12/2015 | Mitsui | A61B 1/0646 |
| | | | | 348/65 |
| 2018/0098690 | A1 | 4/2018 | Iwaki | |
| 2019/0311476 | A1* | 10/2019 | Hayami | A61B 5/7264 |
| 2020/0053296 | A1* | 2/2020 | Endo | H04N 23/60 |
| 2020/0058124 | A1 | 2/2020 | Iwaki | |

FOREIGN PATENT DOCUMENTS

| | | | |
|---|---|---|---|
| WO | 2011/096279 A1 | 8/2011 | |
| WO | 2014/091964 A1 | 6/2014 | |
| WO | 2016/199273 A1 | 12/2016 | |
| WO | 2018/105063 A1 | 6/2018 | |
| WO | WO-2018198161 A1 * | 11/2018 | A61B 1/00009 |

OTHER PUBLICATIONS

International Search Report issued in PCT/JP2020/030875; mailed Oct. 20, 2020.

International Preliminary Report on Patentability and Written Opinion issued in PCT/JP2020/030875; issued Mar. 1, 2022.

\* cited by examiner

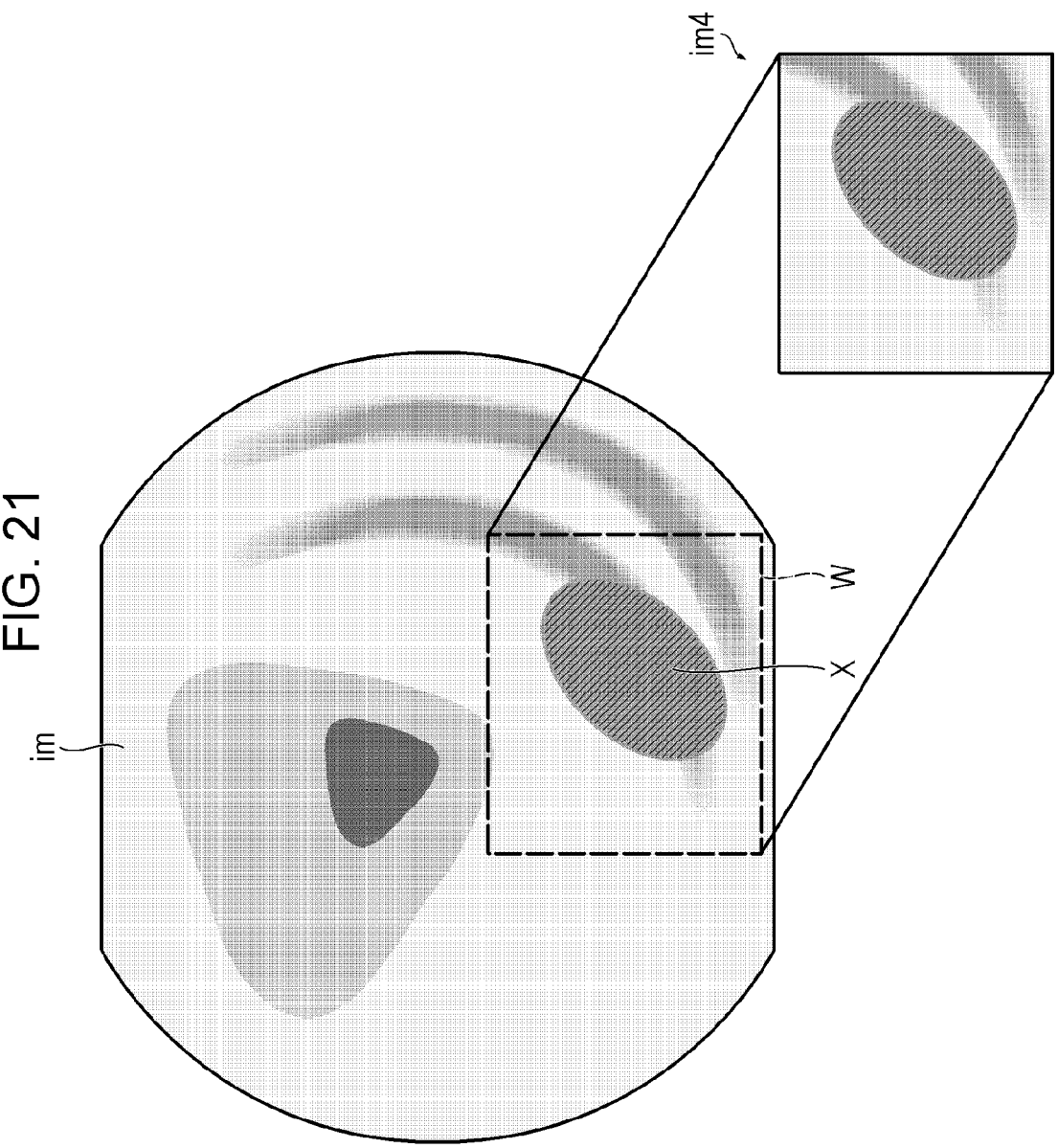

MEDICAL IMAGE PROCESSING SYSTEM AND OPERATION METHOD THEREFOR

CROSS-REFERENCE TO RELATED APPLICATIONS

The present application is a Continuation of PCT International Application No. PCT/JP2020/030875 filed on Aug. 14, 2020 claiming priority under 35 U.S.C § 119(a) to Japanese Patent Application No. 2019-154640 filed on Aug. 27, 2019. Each of the above applications is hereby expressly incorporated by reference, in its entirety, into the present application.

BACKGROUND OF THE INVENTION

1. Field of the Invention

The present invention relates to a medical image processing system and an operation method therefor.

2. Description of the Related Art

A system is known that analyzes an image (endoscopic image) captured by an endoscope, automatically detects a region of interest, and gives a notification.

WO2018/198161A describes a technique in which in a case where a region of interest is detected, visual information for highlighting the position of the region of interest is added to an endoscopic image under observation and displayed and the display form of the visual information is changed in accordance with the time when the region of interest is observed.

WO2018/105063A describes a technique for determining whether a user is identifying a lesion part, and performing a support process for identification only in a case where identification is in progress.

JP2014-161537A describes a technique in which in a case where a region of interest is subjected to a highlighting process, a target to be subjected to the highlighting process is changed in accordance with the amount of movement of the photographic subject.

JP2011-160848A describes a technique for displaying alert information in a case where a region of interest is detected, and changing the display time of the alert information in accordance with the amount of movement of an image.

SUMMARY OF THE INVENTION

In a case where a region of interest is detected, it is important to give the user a notification of the detection. However, notifications successively given even after the user has found a lesion part may hinder the diagnosis, which is a problem. There is another problem that the user may fail to find a lesion part even though the user is given a notification.

The present invention has been made in view of the above-described circumstances, and an object thereof is to provide a medical image processing system with which a notification of detection of a region of interest can be appropriately given and an operation method therefor.

(1) A medical image processing system including: an image obtaining unit that obtains a medical image; a display unit that displays the medical image; a region-of-interest detection unit that detects a region of interest from within the medical image; an amount-of-movement estimation unit that estimates an amount of movement of a device that captures the medical image, on the basis of the medical image; and a notification unit that gives a notification of detection of the region of interest in a case where the region of interest is detected, and changes a form of the notification in accordance with the amount of movement estimated by the amount-of-movement estimation unit after notification.

(2) The medical image processing system according to (1), in which the amount-of-movement estimation unit estimates the amount of movement in a case where the region of interest is detected.

(3) The medical image processing system according to (1) or (2), in which the notification unit gives the notification of detection of the region of interest by highlighting the region of interest in the medical image displayed on the display unit, and changes a degree of highlight of the region of interest in accordance with the amount of movement estimated by the amount-of-movement estimation unit after notification.

(4) The medical image processing system according to (3), in which the notification unit highlights the region of interest by outlining the region of interest by a frame in the medical image displayed on the display unit.

(5) The medical image processing system according to (4), in which the notification unit changes the degree of highlight of the region of interest by changing at least one of a thickness, a line type, a color, a shape, a degree of blinking, or a brightness of the frame.

(6) The medical image processing system according to any one of (3) to (5), in which the notification unit increases the degree of highlight of the region of interest in a case where the amount of movement estimated by the amount-of-movement estimation unit after notification of the region of interest is greater than or equal to a threshold value.

(7) The medical image processing system according to any one of (3) to (6), in which the notification unit decreases the degree of highlight of the region of interest or turns off highlighting of the region of interest in a case where the amount of movement estimated by the amount-of-movement estimation unit after notification of the region of interest is less than a threshold value.

(8) The medical image processing system according to any one of (3) to (5), in which the notification unit increases the degree of highlight of the region of interest in a case where the amount of movement estimated by the amount-of-movement estimation unit after notification of the region of interest is greater than or equal to a first threshold value, and decreases the degree of highlight of the region of interest or turns off highlighting of the region of interest in a case where the amount of movement estimated by the amount-of-movement estimation unit after notification of the region of interest is less than a second threshold value.

(9) The medical image processing system according to (1) or (2), in which the notification unit gives the notification of detection of the region of interest by emitting a sound, and changes at least one of a sound volume, a tone, or a type of the sound in accordance with the amount of movement estimated by the amount-of-movement estimation unit after notification.

(10) A medical image processing system including: an image obtaining unit that obtains a medical image; a region-of-interest detection unit that detects a region of interest from within the medical image; an information generation unit that generates information indicating a result of detection in a case where the region of interest is detected; a storage unit that stores the information generated by the information generation unit; an amount-of-movement estimation unit that estimates, in a case where the region of interest is detected, an amount of movement of a device that captures the medical image, on the basis of the medical image; a display unit that has a first display region and a second display region within a screen; and a display control unit that displays the medical image obtained by the image obtaining unit in the first display region, and in a case where the region of interest is detected and where the amount of movement estimated by the amount-of-movement estimation unit after detection of the region of interest is greater than or equal to a threshold value, displays the information stored in the storage unit in the second display region.

(11) The medical image processing system according to (10), in which the information generation unit generates as the information indicating the result of detection of the region of interest, an image obtained by highlighting the region of interest in the medical image.

(12) The medical image processing system according to (11), in which the information generation unit generates an image obtained by highlighting the region of interest by outlining the region of interest by a frame in the medical image.

(13) The medical image processing system according to (10), in which the information generation unit generates as the information indicating the result of detection of the region of interest, an image obtained by by cutting the region of interest from the medical image.

(14) The medical image processing system according to any one of (1) to (13), in which the amount-of-movement estimation unit estimates the amount of movement at predetermined frame intervals.

(15) The medical image processng system according to (14), in which the amount-of-movement estimation unit estimates the amount of movement on the basis of an amount of shift of an entire image.

(16) The medical image processing system according to (14), in which the amount-of-movement estimation unit estimates the amount of movement on the basis of an amount of shift of the region of interest.

(17) An operation method for a medical image processing system, the operation method including: a step of obtaining a medical image; a step of detecting a region of interest from within the medical image; a step of giving a notification of detection of the region of interest in a case where the region of interest is detected; a step of estimating an amount of movement of a device that captures the medical image in a case where the region of interest is detected; and a step of changing a form of the notification in accordance with the estimated amount of movement.

(18) An operation method for a medical image processing system, the operation method including: a step of obtaining a medical image; a step of displaying the medical image in a first display region set within a screen of a display unit; a step of detecting a region of interest from within the medical image; a step of generating information indicating a result of detection in a case where the region of interest is detected; a step of storing the generated information indicating the result of detection of the region of interest in a storage unit; a step of estimating, in a case where the region of interest is detected, an amount of movement of a device that captures the medical image; and a step of displaying, in a case where the estimated amount of movement is greater than or equal to a threshold value, the information stored in the storage unit in a second display region set within the screen of the display unit.

According to the present invention, a notification of detection of a region of interest can be appropriately given.

BRIEF DESCRIPTION OF THE DRAWINGS

FIG. 21 is a conceptual diagram illustrating generation of a cropped image.

DESCRIPTION OF THE PREFERRED EMBODIMENTS

Hereinafter, preferred embodiments of the present invention will be described in detail with reference to the attached drawings.

First Embodiment

An example case where the present invention is applied to a system (endoscope system) that processes an image (endoscopic image) captured by an endoscope as a medical image will be described below.

System Configuration

Figure 1:
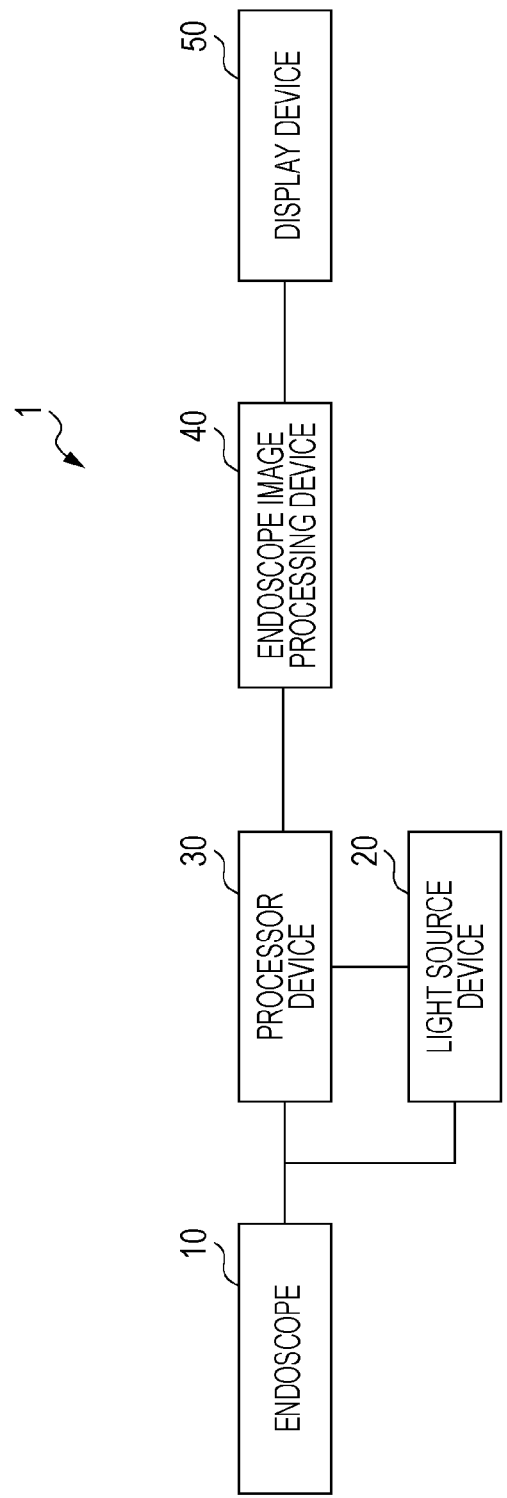
FIG. 1 is a system configuration diagram of an endoscope system according to a first embodiment.

FIG. 1 is a system configuration diagram of an endoscope system according to this embodiment.

As illustrated in FIG. 1, an endoscope system 1 according to this embodiment includes an endoscope 10, a light source device 20, a processor device 30, an endoscope image processing device 40, and a display device 50. The endoscope system 1 is an example of the medical image processing system.

Figure 2:
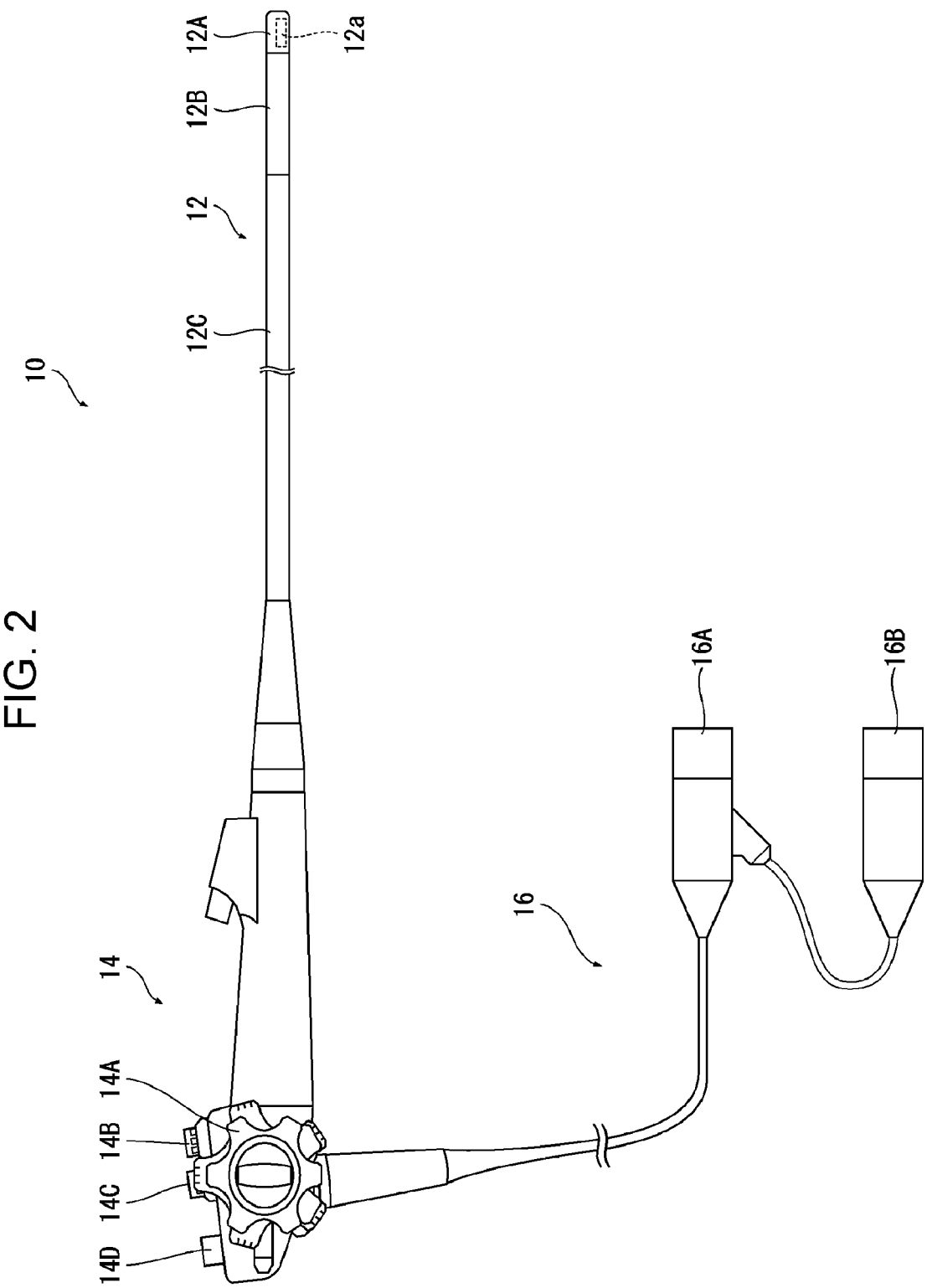
FIG. 2 is a schematic configuration diagram of an endoscope.

FIG. 2 is a schematic configuration diagram of the endoscope 10.

The endoscope 10 is a soft endoscope (electronic endoscope). The endoscope 10 is mainly constituted by an insertion part 12, an operation part 14, and a connection part 16.

The insertion part 12 is mainly constituted by a tip part 12A, a bending part 12B, and a soft part 12C. The tip part 12A includes an observation window, an illumination window, and a nozzle and forceps port on the end surface thereof. The tip part 12A includes an imaging unit 12a in the inside thereof. The imaging unit 12a is constituted by an imaging optical system, an image sensor, and so on. The image sensor is, for example, a color CCD (charge-coupled device) image sensor or a color CMOS (complementary metal-oxide semiconductor) image sensor having, for example, a predetermined color filter arrangement (for example, the Bayer arrangement).

The operation part 14 includes various operating members operated by an operator (user). For example, the operation part 14 includes an angle knob 14A for an angle operation of the bending part 12B, an air/water supply button 14B for an air supply operation and a water supply operation, a suction button 14C for a suction operation, and a shutter button 14D for capturing a still image.

The connection part 16 is formed of a cord having flexibility. The connection part 16 includes a connector 16A for connection to the light source device 20 and a connector 16B for connection to the processor device 30 at the distal end thereof.

The light source device 20 includes a light source and supplies light from the light source to the endoscope 10 as illumination light. The illumination light supplied to the endoscope 10 is emitted through the illumination window included in the tip part 12A. As the light from the light source, for example, white light is used.

The processor device 30 takes in a captured-image signal output from the endoscope 10, performs a predetermined signal process for the captured-image signal, and generates an observation image (endoscopic image) observed by the endoscope 10. The processor device 30 also functions as a control unit for the entire system. The processor device 30 is formed of, for example, a computer that includes a CPU (central processing unit), a ROM (read-only memory), and a RAM (random access memory) and implements a function of generating an endoscopic image, a function of controlling the units of the system, and so on by the CPU executing a predetermined program. The ROM stores various programs executed by the CPU, data necessary for control, and so on. The RAM provides a work memory space for the CPU.

The endoscope image processing device 40 obtains an endoscopic image output from the processor device 30 and displays the endoscopic image on the display device 50. The endoscope image processing device 40 detects a region of interest from the endoscopic image and gives a notification of the detection. The endoscope image processing device 40 is formed of, for example, a computer that includes a CPU, a ROM, and a RAM and functions as an endoscope image processing device by the CPU executing a predetermined program (endoscope image processing program). The ROM stores various programs executed by the CPU, data necessary for control, and so on. The RAM provides a work memory space for the CPU.

Figure 3:
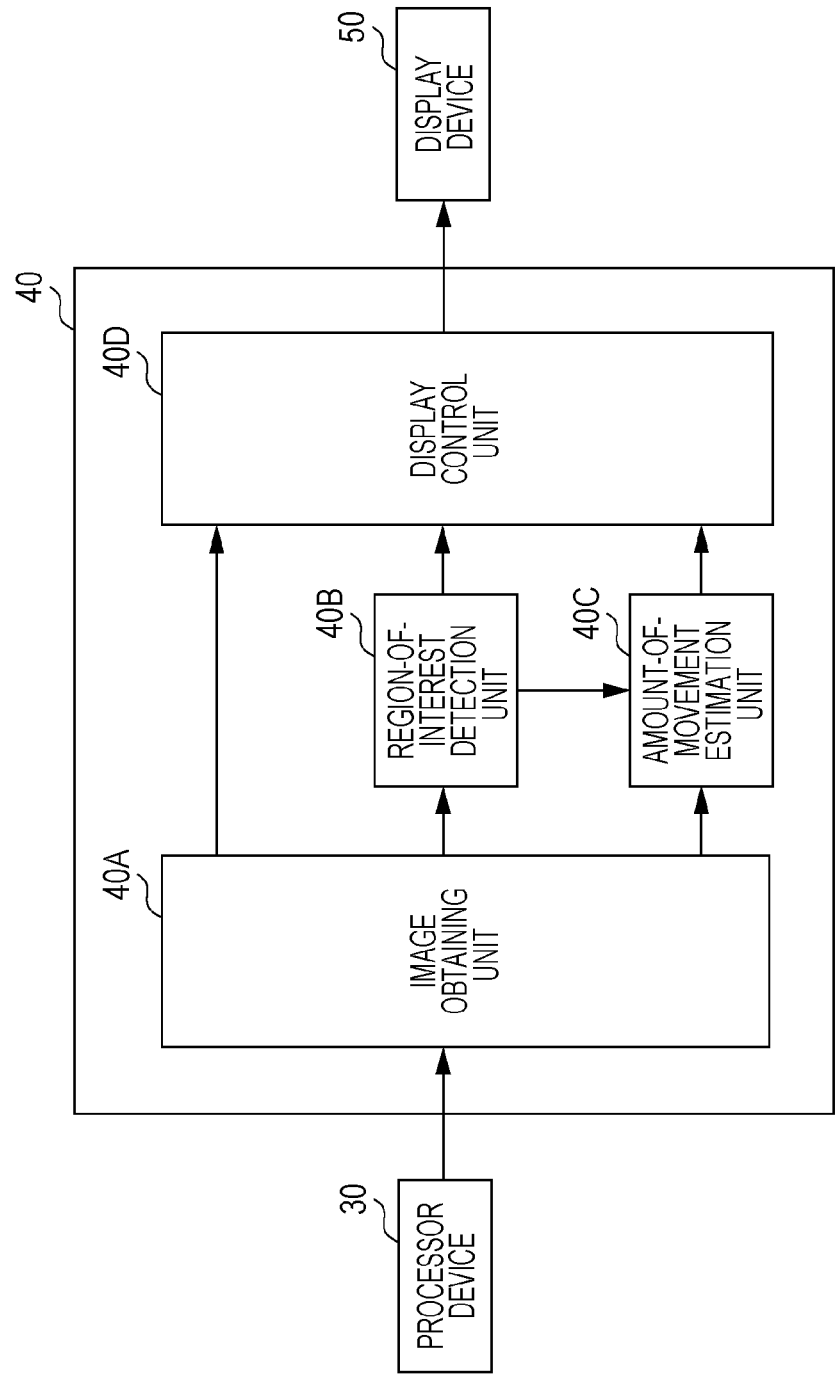
FIG. 3 is a block diagram of the functions of an endoscope image processing device in the endoscope system according to the first embodiment.

FIG. 3 is a block diagram of the functions of the endoscope image processing device.

As illustrated in FIG. 3, the endoscope image processing device 40 has functions of an image obtaining unit 40A that obtains an endoscopic image, a region-of-interest detection unit 40B that detects a region of interest from within the obtained endoscopic image, an amount-of-movement estimation unit 40C that estimates the amount of movement of the endoscope 10 on the basis of the obtained endoscopic image, and a display control unit 40D that controls display of the endoscopic image on the display device 50.

The image obtaining unit 40A takes in an endoscopic image output from the processor device 30. The endoscopic image is an example of a medical image. Image capturing by the endoscope 10 is performed at a predetermined frame rate. Therefore, the image obtaining unit 40A successively takes in time-series endoscopic images.

The region-of-interest detection unit 40B detects a region of interest from within an endoscopic image obtained by the image obtaining unit 40A. Here, "region of interest" refers to a region that is suspected of being a lesion part in the endoscopic image. The region-of-interest detection unit 40B detects a region of interest from within the endoscopic image by, for example, image recognition. In the image recognition, for example, an image recognition model generated by machine learning (for example, deep learning) can be used. In addition, the image recognition can be performed by using a publicly known method.

A region of interest is detected with its position and size identified. The position is obtained as, for example, information about the positions of pixels of the region of interest present in the endoscopic image. The size is obtained as the number of pixels of the region of interest present in the endoscopic image.

The amount-of-movement estimation unit 40C estimates the amount of movement of the endoscope 10 (a device that captures a medical image) on the basis of an endoscopic image obtained by the image obtaining unit 40A. More specifically, the amount-of-movement estimation unit 40C estimates the amount of movement of the tip part 12A, including the imaging unit 12a, of the insertion part 12 of the endoscope 10. Here, "movement" includes movement associated with rotation of the tip part 12A and movement associated with a change in the orientation of the tip part 12A, in addition to movement associated with movement of the tip part 12A. Further, "amount of movement" is a value that indicates the magnitude of movement of the tip part 12A of the endoscope 10.

The amount-of-movement estimation unit 40C estimates the amount of movement of the endoscope at predetermined frame intervals. The amount-of-movement estimation unit 40C estimates the amount of movement of the endoscope on the basis of the amount of shift of the entire image. For example, in a case where the amount of movement of the endoscope is estimated on a per frame basis, the amount-of-movement estimation unit 40C detects the amount of shift of the entire image for each frame by a comparison with the immediately preceding frame image. For example, in a case where the obtained image is the image of an N-th frame, the amount-of-movement estimation unit 40C detects the amount of shift of the entire image by a comparison with the image of an N-1-th frame. The amount-of-movement estimation unit 40C estimates the amount of movement of the endoscope between the frames on the basis of the detected amount of shift of the entire image.

The amount of shift of the entire image is detected, for example, as follows. First, a set of corresponding feature points in two successive frames are extracted from the entire image. On the basis of the positional relationship between the extracted feature points, a motion vector that indicates the orientation and magnitude of shift of the entire image is obtained. The magnitude of the obtained motion vector is obtained as the amount of shift. In a case where a plurality of sets of feature points are extracted, the average of the magnitudes of motion vectors obtained from the respective sets of feature points is calculated and obtained as the amount of shift of the entire image.

In a case where a region of interest is detected by the region-of-interest detection unit 40B, the amount-of-movement estimation unit 40C estimates the amount of movement of the endoscope 10 on the basis of the endoscopic image obtained by the image obtaining unit 40A. That is, when a region of interest is detected, an estimation process for the amount of movement starts. Therefore, in a case where a region of interest is not detected, the estimation process for the amount of movement is not performed. As described above, when the estimation process for the amount of movement is performed only in a case where a region of interest is detected, a processing load (including a computational load) in the endoscope image processing device 40 can be reduced. When a region of interest is detected by the region-of-interest detection unit 40B, the amount-of-movement estimation unit 40C is notified of detection of the region of interest. In response to this notification of detection, which serves as a trigger, the amount-of-movement estimation unit 40C starts the estimation process for the amount of movement.

The display control unit 40D controls display of an endoscopic image on the display device 50. The display control unit 40D displays an endoscopic image obtained by the image obtaining unit 40A on the display device 50 as is in a state where a region of interest is not detected. On the other hand, in a case where a region of interest is detected, the display control unit 40D displays an image in which the region of interest is highlighted.

Figure 4:
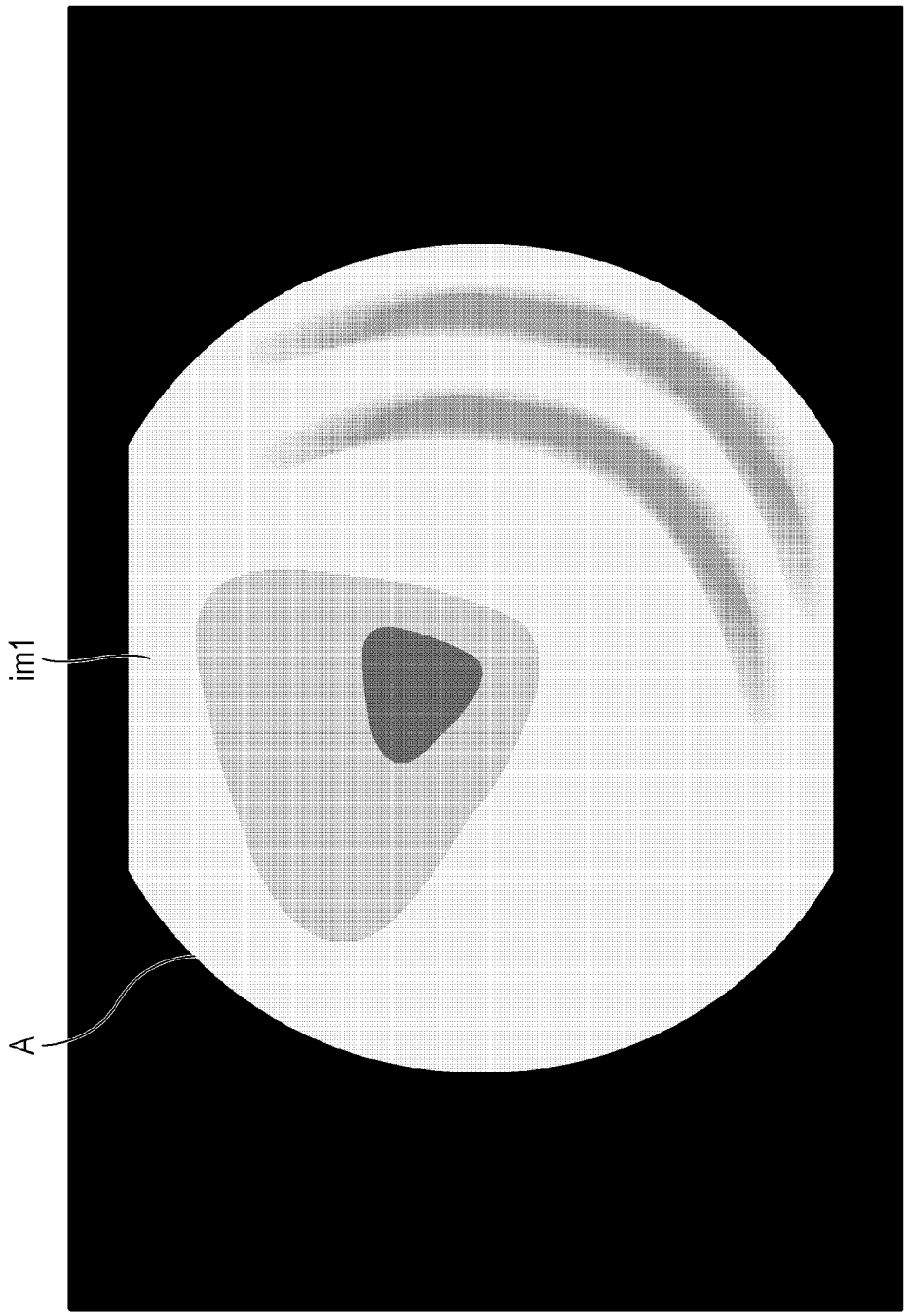
FIG. 4 is a diagram illustrating an example display image in a case where a region of interest is not detected.
Figure 5:
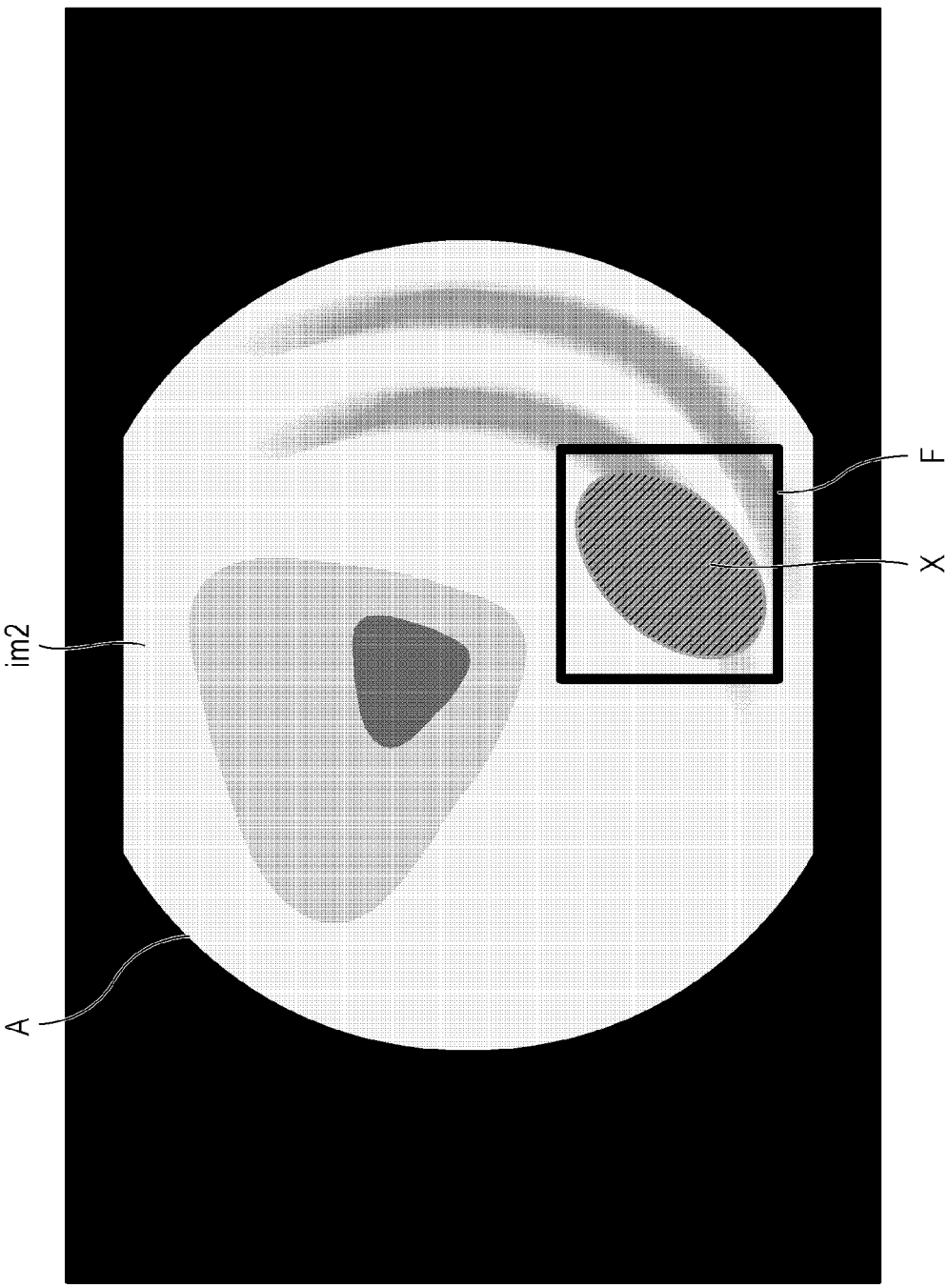
FIG. 5 is a diagram illustrating an example display image in a case where a region of interest is detected.

FIG. 4 is a diagram illustrating an example display image in a case where a region of interest is not detected. FIG. 5 is a diagram illustrating an example display image in a case where a region of interest is detected.

As illustrated in FIG. 4, in a state where a region of interest is not detected, an endoscopic image im1 captured by the endoscope 10 is displayed as is. The endoscopic image im1 is displayed in a predetermined display region A set within the screen.

On the other hand, in a case where a region of interest is detected, an endoscopic image im2 in which the region of interest (the hatched elliptic region in FIG. 5) X is highlighted in the image is displayed as illustrated in FIG. 5. The endoscopic image im2 is displayed in the predetermined display region A set within the screen. The endoscopic image im2 in which the region of interest X is highlighted is generated by outlining the region of interest X by a rectangular frame F in the image. The endoscopic image im2 in which the frame F is displayed is displayed on the display device 50 to thereby give a notification that the region of interest is detected.

In a case where a region of interest is detected, the display control unit 40D displays the frame F with a predetermined line thickness (first thickness that is a reference). Thereafter, the display control unit 40D changes the degree of highlight (which is synonymous with the strength of highlight) of the frame F in accordance with the amount of movement of the endoscope 10 estimated by the amount-of-movement estimation unit 40C. That is, the display control unit 40D changes the line thickness of the frame F. Specifically, in a case where the amount of movement of the endoscope 10 estimated by the amount-of-movement estimation unit 40C is greater than or equal to a predetermined threshold value, the display control unit 40D changes the line thickness of the frame F to a second thickness thicker than the first thickness (first thickness<second thickness).

Figure 6:
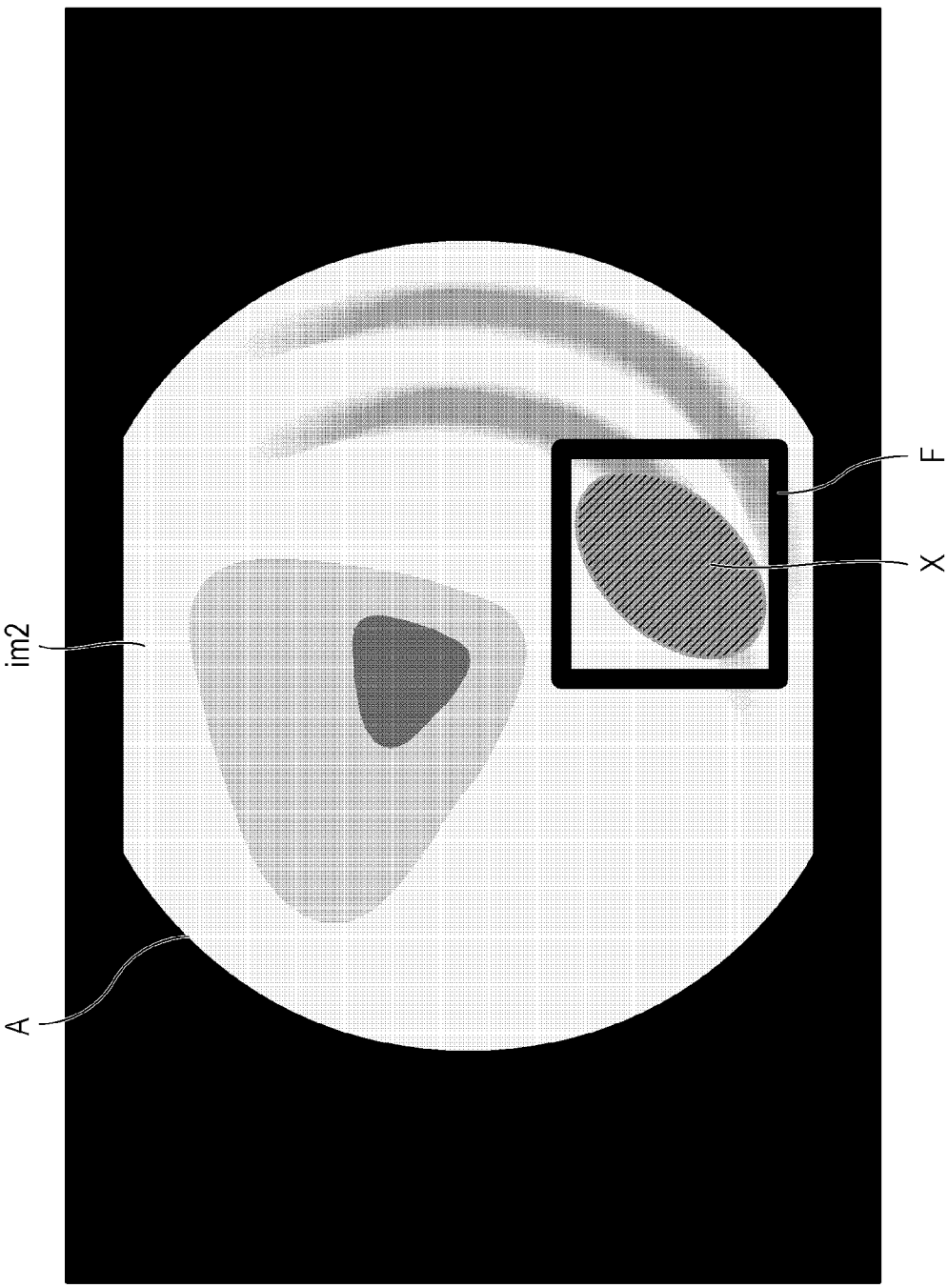
FIG. 6 is a diagram illustrating an example display image in a case where the amount of movement of the endoscope estimated by an amount-of-movement estimation unit is greater than or equal to a threshold value.

FIG. 6 is a diagram illustrating an example display image in a case where the amount of movement of the endoscope estimated by the amount-of-movement estimation unit is greater than or equal to the threshold value.

As illustrated in FIG. 6, when the amount of movement of the endoscope 10 estimated by the amount-of-movement estimation unit 40C becomes greater than or equal to the threshold value after display of the frame F, the line thickness of the frame F that outlines the region of interest X increases, and the degree of highlight is increased.

The display control unit 40D is an example of a notification unit and displays the frame in an endoscopic image displayed on the display device 50 to thereby notify the operator of detection of the region of interest. In this example, the region of interest is outlined by the frame to thereby also give a notification of the result of detection of the region of interest (position and size).

The display device 50 is formed of, for example, a display, such as a liquid crystal display or an organic EL (organic electroluminescent, OEL) display. The display device 50 is an example of a display unit.

Operations

Operations (operation method) of the endoscope system 1 according to this embodiment will be described below. In the endoscope system 1 according to this embodiment, when an image is captured by the endoscope 10, the captured image (endoscopic image) is displayed on the display device 50 (see FIG. 4). From the captured endoscopic image, a region of interest is detected. When a region of interest is detected, the region of interest is outlined by a frame in the display image to thereby give a notification of detection (see FIG. 5). After notification of detection of the region of interest is given, the form of notification is changed in accordance with the amount of movement of the endoscope 10 thereafter. That is, the degree of highlight of the frame is changed. Operations from detection of a region of interest to notification and operations after notification will be described below.

Figure 7:
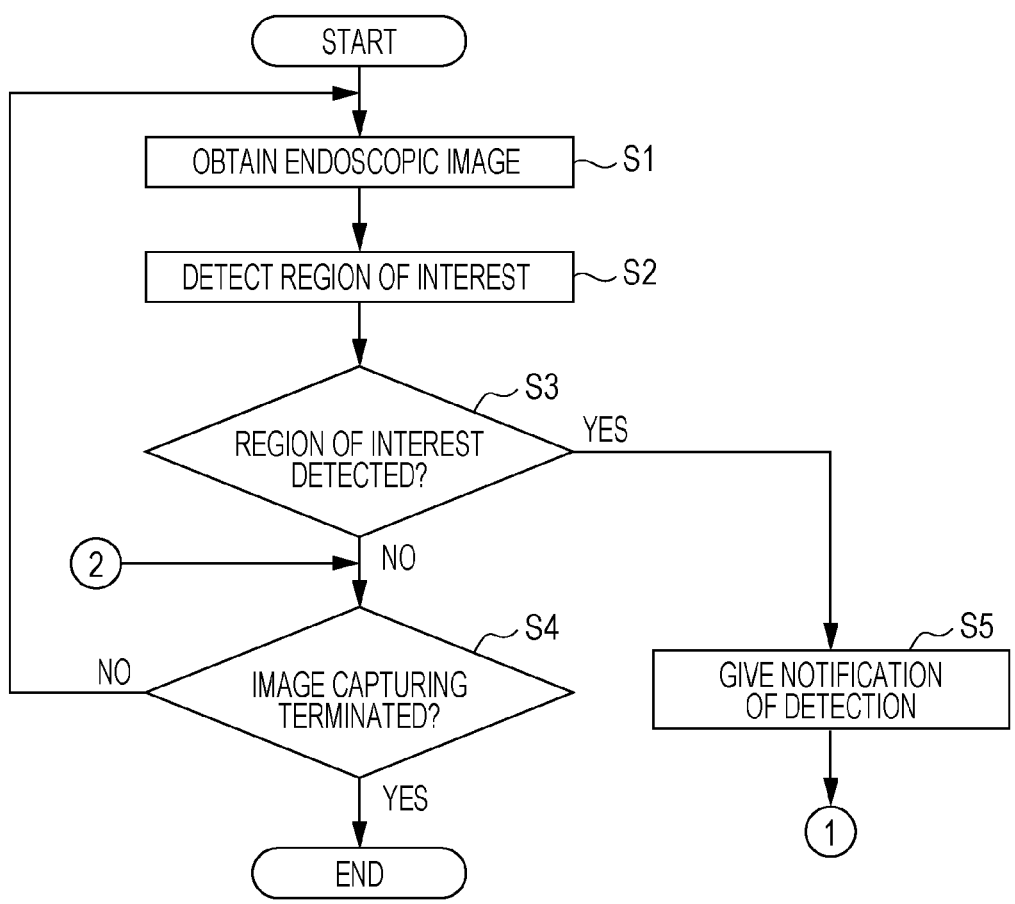
FIG. 7 is a flowchart illustrating a processing procedure from detection of a region of interest to notification.

FIG. 7 is a flowchart illustrating a processing procedure from detection of a region of interest to notification.

As illustrated in FIG. 7, an endoscopic image captured by the endoscope 10 is first obtained (step S1). Next, detection of a region of interest is performed (step S2). That is, on the basis of the obtained endoscopic image, detection of a region of interest from within the image is performed. Next, on the basis of the result of detection of a region of interest, it is determined whether a region of interest is detected (step S3).

In a case where no region of interest is detected (in a case of NO in step S3), it is subsequently determined whether image capturing is terminated (step S4). Determination as to whether image capturing is terminated is performed on the basis of whether an endoscopic image of the next frame is present. In a case where an endoscopic image of the next frame is not obtained by the image obtaining unit 40A, it is determined that image capturing is terminated. In a case where image capturing is terminated (in a case of YES in step S4), the process ends. On the other hand, in a case where image capturing is not terminated (in a case of NO in step S4), the flow returns to step S1, and the next frame image is obtained.

In a case where a region of interest is detected (in a case of YES in step S3), a notification of detection of the region of interest is given (step S5). That is, as illustrated in FIG. 5, the region of interest X outlined by the frame F in the currently displayed endoscopic image is displayed. At this time, the frame F is displayed with the first thickness (reference thickness).

Figure 8:
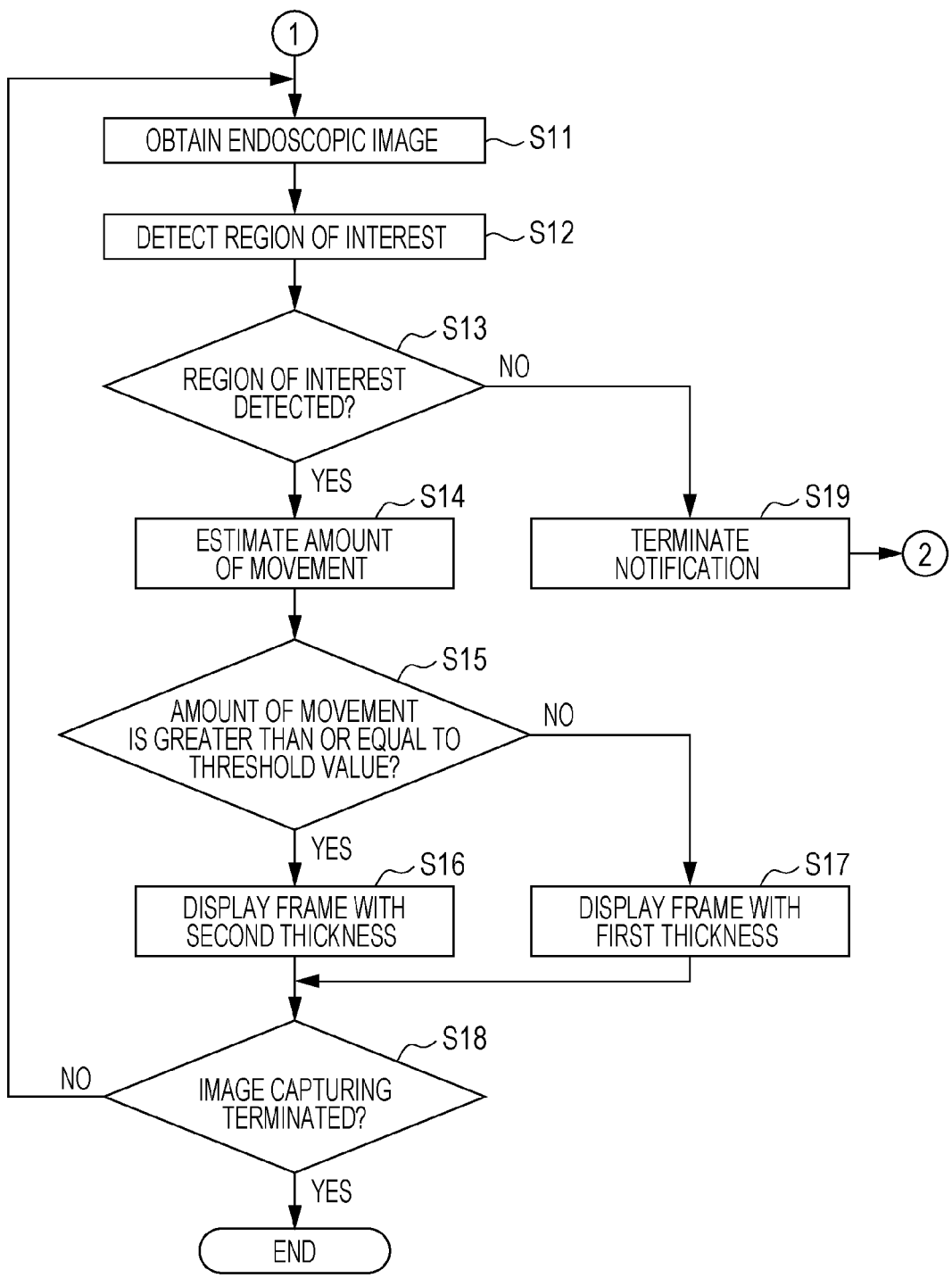
FIG. 8 is a flowchart illustrating a processing procedure after notification of detection of a region of interest.

FIG. 8 is a flowchart illustrating a processing procedure after notification of detection of a region of interest.

After notification, an endoscopic image of the next frame is first obtained (step S11). Next, detection of a region of interest is performed (step S12). Next, on the basis of the result of detection of a region of interest, it is determined whether a region of interest is detected (step S13).

In a case where no region of interest is detected (in a case of NO in step S13), notification is terminated (step S19). That is, display of the frame F is erased (highlighting of the region of interest is turned off).

On the other hand, in a case where a region of interest is detected (in a case of YES in step S13), the amount of movement of the endoscope 10 is estimated from the image (step S14). The estimated amount of movement is compared with a threshold value, and it is determined whether the estimated amount of movement is greater than or equal to the threshold value (step S15). The threshold value is determined in advance.

In a case where the estimated amount of movement is greater than or equal to the threshold value (in a case of YES in step S15), the frame F that outlines the region of interest X is displayed with the second thickness as illustrated in FIG. 6 (step S16). That is, the frame F is displayed with an increased degree of highlight.

On the other hand, in a case where the estimated amount of movement is less than the threshold value (in a case of NO in step S15), the frame F is displayed with the first thickness (step S17). That is, as illustrated in FIG. 5, the frame F is displayed without increasing the degree of highlight.

Subsequently, it is determined whether image capturing is terminated (step S18). In a case where image capturing is terminated (in a case of YES in step S18), the process ends. In a case where image capturing is not terminated (in a case of NO in step S18), the flow returns to step S11, and an endoscopic image of the next frame is obtained.

As described above, with the endoscope system 1 according to this embodiment, the display form of the frame F for notification of detection of a region of interest is changed in accordance with the amount of movement of the endoscope 10 after detection. That is, in a case where the amount of movement is large, the frame F is displayed with an increased degree of highlight.

In a case where an operator finds a lesion part, the operator usually observes the lesion part closely, and therefore, the endoscope 10 tends to move to a small degree. On the other hand, in a case where the operator is searching for a lesion part, the endoscope 10 tends to move to a large degree because the operator continuously performs observation so as not to overlook a lesion part.

In a case where a region of interest is automatically detected and where the endoscope 10 moves to a large degree, it is assumed that the operator fails to notice the region of interest when the endoscope 10 passes by the region of interest. Therefore, in such a case, the degree of highlight is increased so as to prevent an oversight. Accordingly, a notification of detection of the region of interest can be appropriately given.

With the endoscope system 1 according to this embodiment, the estimation process for the amount of movement is performed only in a case where a region of interest is detected. Accordingly, a processing load can be reduced, and diagnosis can be made more smoothly.

Note that in a case where, for example, a processing load need not be taken into consideration, a configuration can be employed in which the amount of movement of the endoscope is estimated continuously from the start of image capturing.

Modifications of Endoscope System according to First Embodiment

[1] Modification of the Method for Changing the Degree of Highlight in a Case where a Region of Interest is Highlighted with a Frame In the above-described embodiment, a configuration is employed in which the degree of highlight is changed by changing the line thickness of the frame; however, the method for changing the degree of highlight is not limited to this. In addition, for example, the degree of highlight of a region of interest can be changed by changing, for example, the line type, color, shape, degree of blinking, and brightness of the frame.

Here, a case where the degree of highlight is changed by changing the line type of the frame is, for example, a case where, for example, a dashed line is set as a reference line type (a line type initially displayed in a case where a region of interest is detected) and the dashed line is changed to a solid line in a case where the amount of movement greater than or equal to the threshold value is estimated. Alternatively, an example case is possible where a solid line is set as the reference line type and the solid line is changed to a double line in a case where the amount of movement greater than or equal to the threshold value is estimated.

A case where the degree of highlight is changed by changing the color of the frame is, for example, a case where the color of the frame is changed to a color that is visually recognized more easily (conspicuous color). An example form is possible where a white color is set as a reference color (a color of the frame initially displayed in a case where a region of interest is detected) and the white color is changed to a red color or a yellow color in a case where the amount of movement greater than or equal to the threshold value is estimated.

A case where the degree of highlight is changed by changing the shape of the frame is, for example, a case where the shape of the frame is changed to a shape that is visually recognized more easily (conspicuous shape).

Figure 9B:
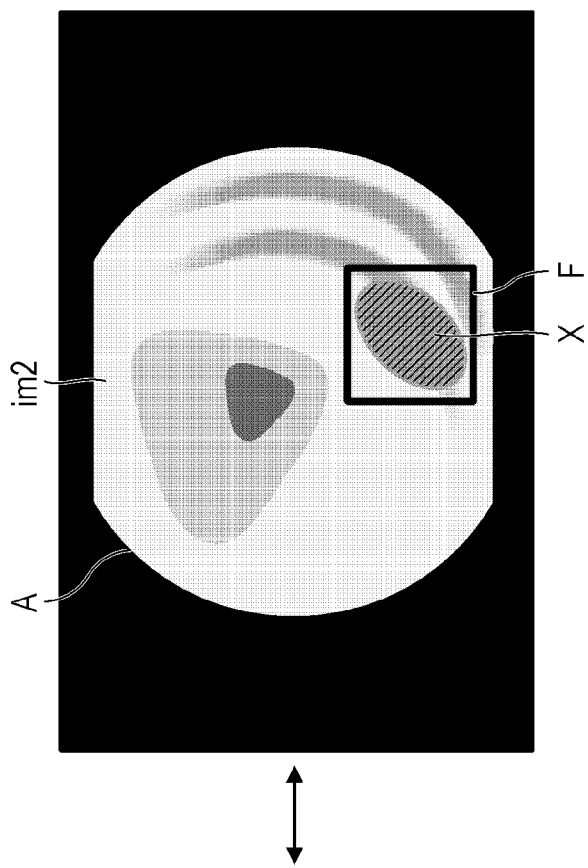
FIGS. 9A and 9B are diagrams illustrating example display images in a case where the degree of highlight is changed by changing the shape of a frame.
Figure 9A:
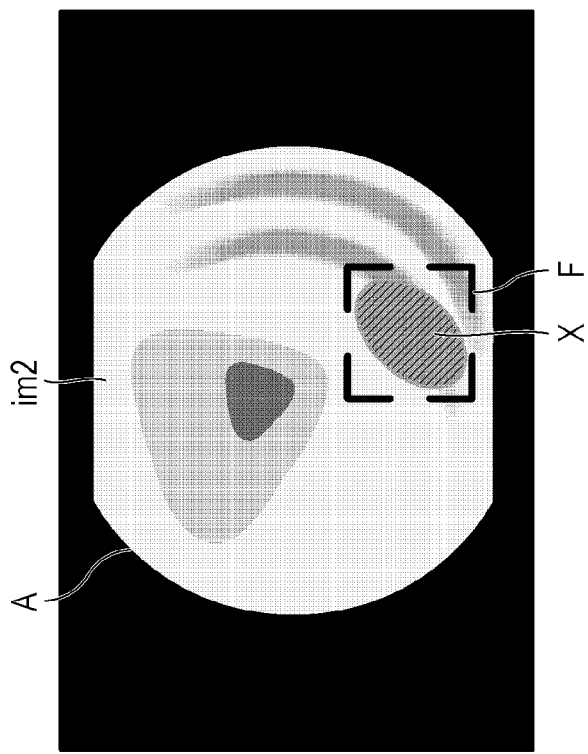

FIGS. 9A and 9B are diagrams illustrating example display images in a case where the degree of highlight is changed by changing the shape of the frame. FIG. 9A illustrates an example image displayed on the display device 50 in a case where a region of interest is detected and FIG. 9B illustrates an example image displayed on the display device 50 in a case where the amount of movement after detection of the region of interest is greater than or equal to the threshold value.

As illustrated in FIG. 9A, the frame F that outlines only the four corners of the rectangular shape (frame having a reference shape) is displayed in a case where the region of interest X is detected from within the endoscopic image. On the other hand, in a case where the amount of movement greater than or equal to the threshold value is estimated after display of the frame having the reference shape, the frame F having the reference shape is changed to the frame F having a shape so as to completely surround the region of interest X as illustrated in FIG. 9B.

Changing the degree of blinking refers to changing the rate of blinking (blinking rate) in a case where a blinking frame is displayed. For example, in a case where a region of interest is detected, the frame that blinks at a first blinking rate (reference blinking rate) is displayed. In a case where the amount of movement greater than or equal to the threshold value is estimated, the frame that blinks at a second blinking rate higher than the first blinking rate is displayed. In addition, for example, an example form is possible where the frame that does not blink is displayed in a case where a region of interest is detected and the frame that blinks is displayed in a case where the amount of movement greater than or equal to the threshold value is estimated.

A case where the degree of highlight is changed by changing the brightness of the frame is a case where, for example, the frame is displayed with a first brightness (reference brightness) in a case where a region of interest is detected and the frame is displayed with a second brightness higher than the first brightness in a case where the amount of movement greater than or equal to the threshold value is estimated.

Those described above can be combined and used. For example, the degree of highlight of a region of interest can be changed by changing the thickness and brightness of the frame. Further, for example, the degree of highlight of a region of interest can be changed by changing the thickness and degree of blinking of the frame. The degree of highlight of a region of interest can be changed by changing the thickness, brightness, and degree of blinking of the frame.

[2] Modifications of the Method for Changing the Degree of Highlight in Accordance with the Amount of Movement In the above-described embodiment, a configuration is employed in which the estimated amount of movement is compared with the threshold value and the degree of highlight is increased (the frame is made thicker) in a case where the estimated amount of movement is greater than or equal to the threshold value; however, the method for changing the degree of highlight in accordance with the amount of movement is not limited to this. Modifications of the method for changing the degree of highlight in accordance with the amount of movement will be described below.

(a) First Modification of the Method for Changing the Degree of Highlight in Accordance with the Amount of Movement In this modification, the degree of highlight of a region of interest is decreased in a case where the amount of movement of the endoscope is less than a threshold value. That is, the line thickness of the frame F is made thinner A processing procedure in a case of displaying an endoscopic image with this method will be described below. Note that the processing procedure from detection of a region of interest to notification is the same as that in the above-described embodiment (see FIG. 7). Therefore, only the process after notification will be described below.

Figure 10:
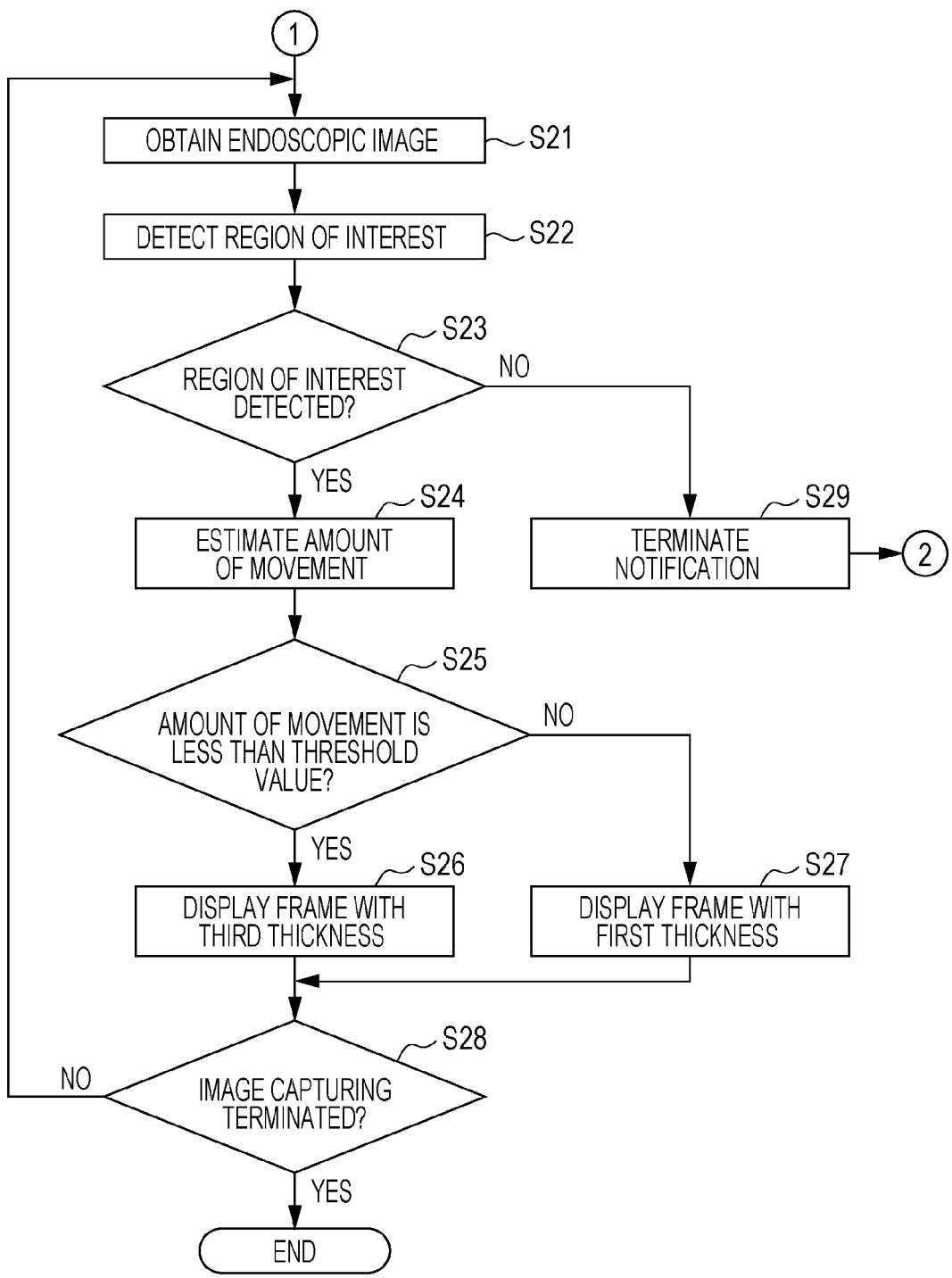
FIG. 10 is a flowchart illustrating a modification of the processing procedure after notification of detection of a region of interest.

FIG. 10 is a flowchart illustrating the processing procedure after notification of detection of a region of interest according to this modification.

After notification, an endoscopic image of the next frame is first obtained (step S21). Next, detection of a region of interest is performed (step S22). Next, on the basis of the result of detection of a region of interest, it is determined whether a region of interest is detected (step S23).

In a case where no region of interest is detected (in a case of NO in step S23), notification is terminated (step S29). That is, display of the frame F is erased (highlighting of the region of interest is turned off).

On the other hand, in a case where a region of interest is detected (in a case of YES in step S23), the amount of movement of the endoscope 10 is estimated from the image (step S24). The estimated amount of movement is compared with a threshold value, and it is determined whether the estimated amount of movement is less than the threshold value (step S25). The threshold value is determined in advance.

Figure 11:
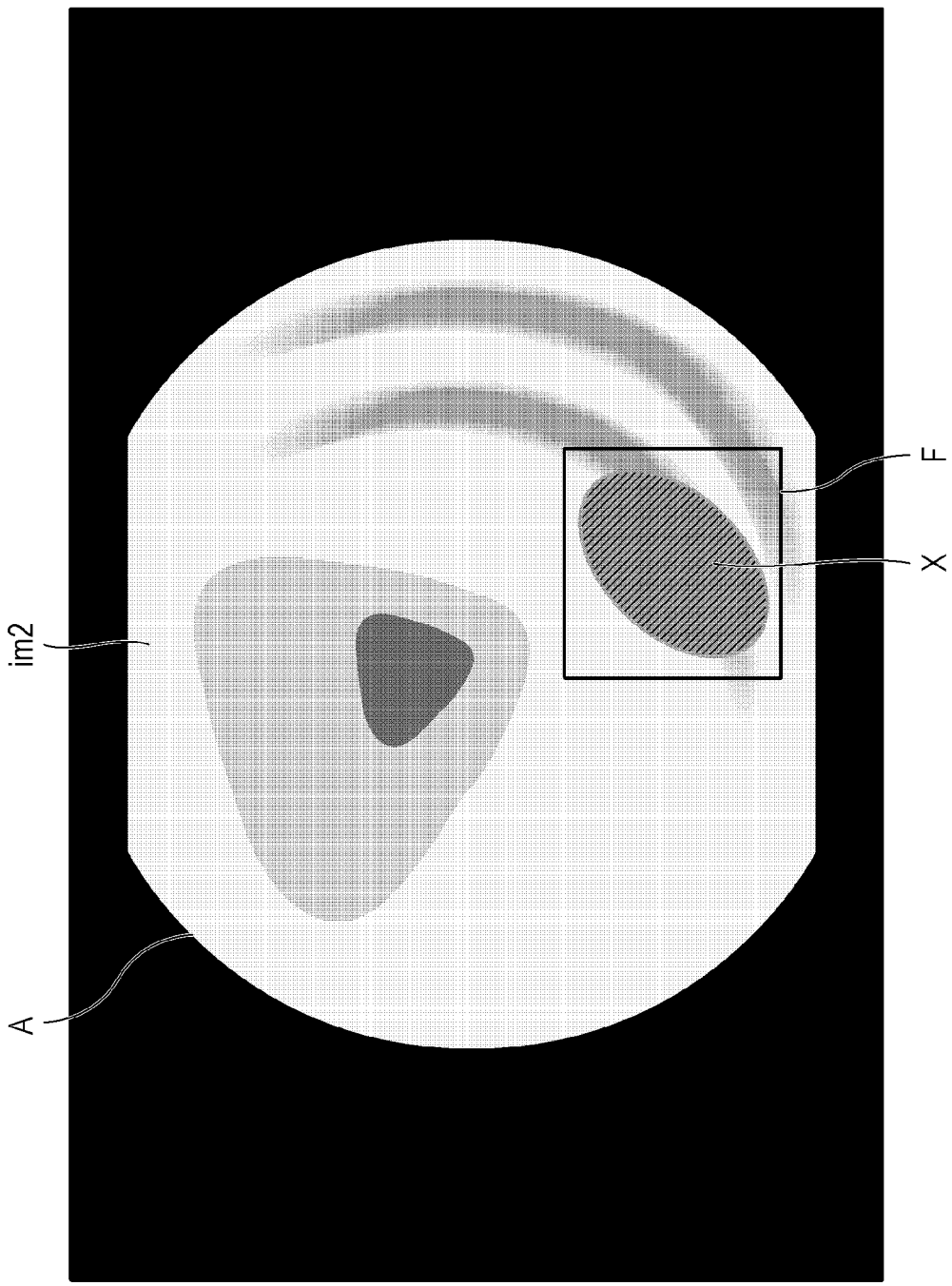
FIG. 11 is a diagram illustrating an example image displayed on a display device in a case where the amount of movement is less than a threshold value.

In a case where the estimated amount of movement is less than the threshold value (in a case of YES in step S25), the frame F that outlines the region of interest X is displayed with a third thickness (step S26). The third thickness is thinner than the first thickness (third thickness<first thickness). FIG. 11 is a diagram illustrating an example image displayed on the display device in a case where the amount of movement is less than the threshold value. As illustrated in FIG. 11, the thickness of the frame F that outlines the region of interest X is made thinner, and the degree of highlight is decreased.

On the other hand, in a case where the estimated amount of movement is greater than or equal to the threshold value (in a case of NO in step S25), the frame F is displayed with the first thickness (step S27). That is, as illustrated in FIG. 5, the frame F is displayed without decreasing the degree of highlight.

Subsequently, it is determined whether image capturing is terminated (step S28). In a case where image capturing is terminated (in a case of YES in step S28), the process ends. In a case where image capturing is not terminated (in a case of NO in step S28), the flow returns to step S21, and an endoscopic image of the next frame is obtained.

As described above, in this modification, the degree of highlight of a region of interest is decreased (the frame line that outlines the region of interest is made thinner) in a case where the amount of movement of the endoscope after the region of interest is highlighted and displayed is small. As described above, in a case where an operator finds a lesion part, the operator observes the lesion part closely, and therefore, the endoscope 10 tends to move to a small degree. In a case where the endoscope 10 moves to a small degree after detection of a region of interest, it is considered that the operator also notices the region of interest. Therefore, successive notifications with the same strength in a case where the endoscope 10 moves to a small degree after detection of the region of interest can result in a decrease in the operator's concentration. Therefore, in a case where the amount of movement of the endoscope becomes small after detection of the region of interest, the degree of highlight of the region of interest is decreased. Accordingly, a notification of detection of the region of interest can be appropriately given.

In this example, a configuration is employed in which the degree of highlight is decreased (the frame line is made thinner) in a case where the estimated amount of movement is less than the threshold value; however, another configuration can be employed in which highlight display is turned off (the frame is erased to terminate notification).

Further, in this example, an example has been described where the degree of highlight is changed by changing the line thickness of the frame; however, the degree of highlight can be changed by changing, for example, the line type of the frame, the degree of blinking of the frame, or the brightness of the frame.

(b) Second Modification of the Method for Changing the Degree of Highlight in Accordance with the Amount of Movement In this modification, the degree of highlight of a region of interest is increased in a case where the amount of movement of the endoscope is greater than or equal to a first threshold value and the degree of highlight of a region of interest is decreased in a case where the amount of movement of the endoscope is less than a second threshold value. Note that the processing procedure from detection of a region of interest to notification is the same as that in the above-described embodiment (see FIG. 7). Therefore, only the process after notification will be described below.

Figure 12:
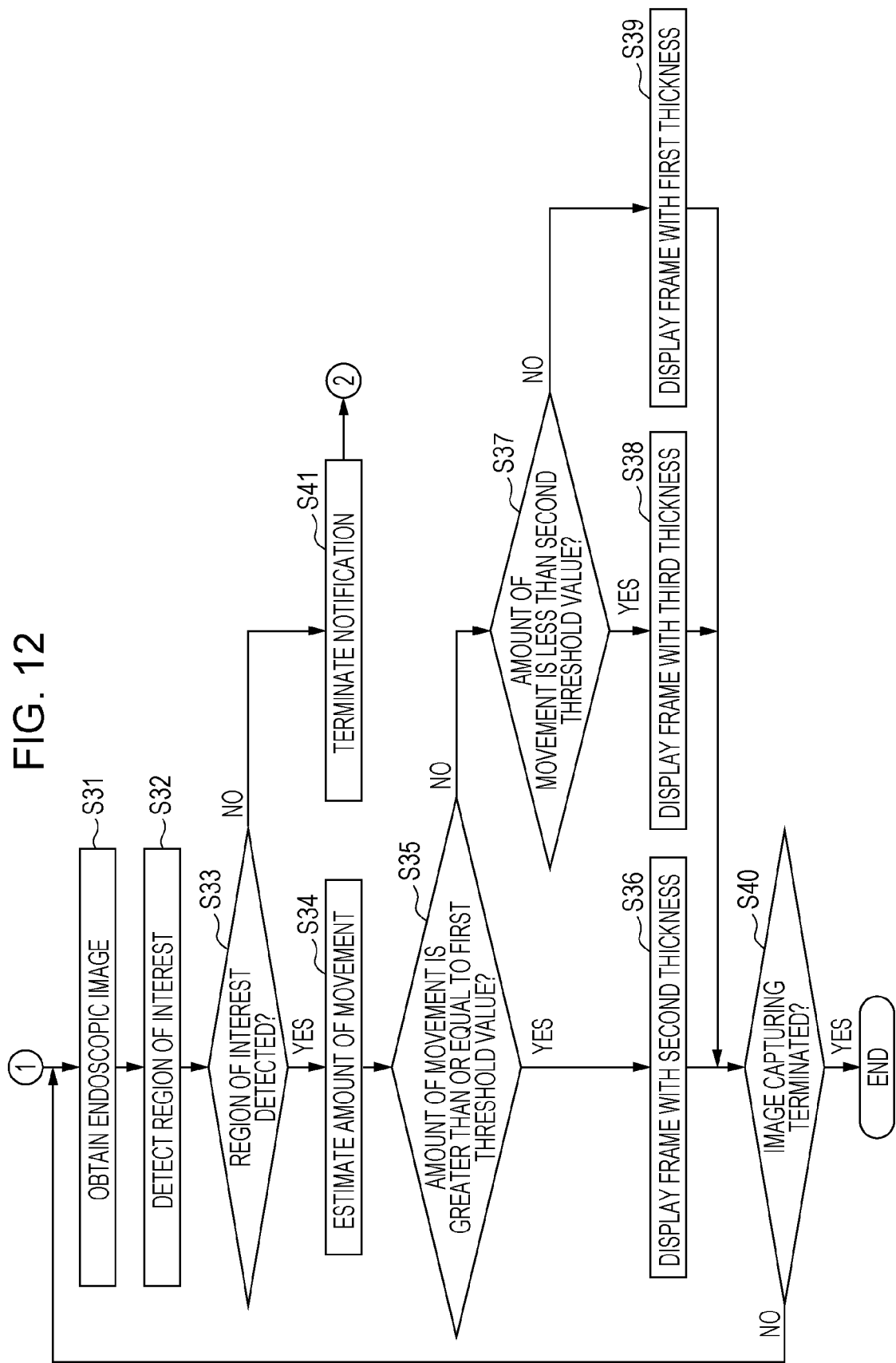
FIG. 12 is a flowchart illustrating a modification of the processing procedure after notification of detection of a region of interest.

FIG. 12 is a flowchart illustrating the processing procedure after notification of detection of a region of interest according to this modification.

An endoscopic image is first obtained (step S31). Next, detection of a region of interest is performed (step S32). Next, on the basis of the result of detection of a region of interest, it is determined whether a region of interest is detected (step S33).

In a case where no region of interest is detected (in a case of NO in step S33), notification is terminated (step S41). That is, display of the frame F is erased (highlighting of the region of interest is turned off).

On the other hand, in a case where a region of interest is detected (in a case of YES in step S33), the amount of movement of the endoscope 10 is estimated from the image (step S34). The estimated amount of movement is compared with a first threshold value, and it is determined whether the estimated amount of movement is greater than or equal to the first threshold value (step S35). The first threshold value is determined in advance.

In a case where the estimated amount of movement is greater than or equal to the first threshold value (in a case of YES in step S35), the frame F that outlines the region of interest X is displayed with the second thickness (first thickness<second thickness) (step S36). That is, as illustrated in FIG. 6, the region of interest X is outlined by the frame F with an increased thickness and displayed, and the degree of highlight of the region of interest X is increased.

On the other hand, in a case where the estimated amount of movement is less than the first threshold value (in a case of NO in step S35), the estimated amount of movement is compared with a second threshold value, and it is determined whether the estimated amount of movement is less than the second threshold value (step S37). The second threshold value is determined in advance. The second threshold value is set to a value smaller than the first threshold value (second threshold value<first threshold value).

In a case where the estimated amount of movement is less than the second threshold value (in a case of YES in step S37), the frame F that outlines the region of interest X is displayed with the third thickness (third thickness<first thickness) (step S38). That is, as illustrated in FIG. 11, the region of interest X is outlined by the frame F with a decreased thickness and displayed, and the degree of highlight of the region of interest X is decreased.

On the other hand, in a case where the estimated amount of movement is greater than or equal to the second threshold value (in a case of NO in step S37), the frame F that outlines the region of interest X is displayed with the first thickness (third thickness<first thickness<second thickness) (step S39). That is, as illustrated in FIG. 5, the degree of highlight is not changed, and the frame F is displayed with the reference thickness (first thickness).

Subsequently, it is determined whether image capturing is terminated (step S40). In a case where image capturing is terminated (in a case of YES in step S40), the process ends. In a case where image capturing is not terminated (in a case of NO in step S40), the flow returns to step S31, and the next endoscopic image is obtained.

As described above, in this modification, the amount of movement of the endoscope 10 is estimated after a region of interest is highlighted and displayed. In a case where the estimated amount of movement of the endoscope 10 is large, the degree of highlight is increased (the line of the frame F is made thicker). In a case where the estimated amount of movement of the endoscope 10 is small, the degree of highlight is decreased (the line of the frame F is made thinner).

In a case where a region of interest is automatically detected and where the endoscope 10 moves to a large degree, it is assumed that the operator fails to notice the region of interest when the endoscope 10 passes by the region of interest. Therefore, in this case, the degree of highlight is increased so as to prevent an oversight. On the other hand, in a case where the endoscope 10 moves to a small degree after detection of a region of interest, it is assumed that the operator also notices the region of interest. Therefore, in this case, the degree of highlight is decreased so as to prevent a decrease in the operator's concentration. Accordingly, a notification of detection of the region of interest can be appropriately given.

In this example, a configuration is employed in which the degree of highlight is decreased (the frame line is made thinner) in a case where the estimated amount of movement is less than the second threshold value; however, another configuration can be employed in which highlight display is turned off (the frame is erased).

Further, in this example, an example has been described where the degree of highlight is changed by changing the line thickness of the frame; however, the degree of highlight can be changed by changing, for example, the line type of the frame, the degree of blinking of the frame, or the brightness of the frame.

(c) Third Modification of the Method for Changing the Degree of Highlight in Accordance with the Amount of Movement In the above-described embodiment, a configuration is employed in which the degree of highlight is changed in two stages; however, another configuration can be employed in which the degree of highlight is changed in multiple stages more than two stages. That is, a configuration can be employed in which the degree of highlight is changed in stages in accordance with the amount of movement of the endoscope 10. For example, in a case where the line thickness of the frame is changed to thereby change the degree of highlight, the line thickness of the frame can be changed in stages in accordance with the amount of movement.

Second Embodiment

Configuration

In this embodiment, in a case where a region of interest is detected from within an endoscopic image, the operator is notified of the detection by sound. After notification, the sound volume is changed in accordance with the amount of movement of the endoscope.

Figure 13:
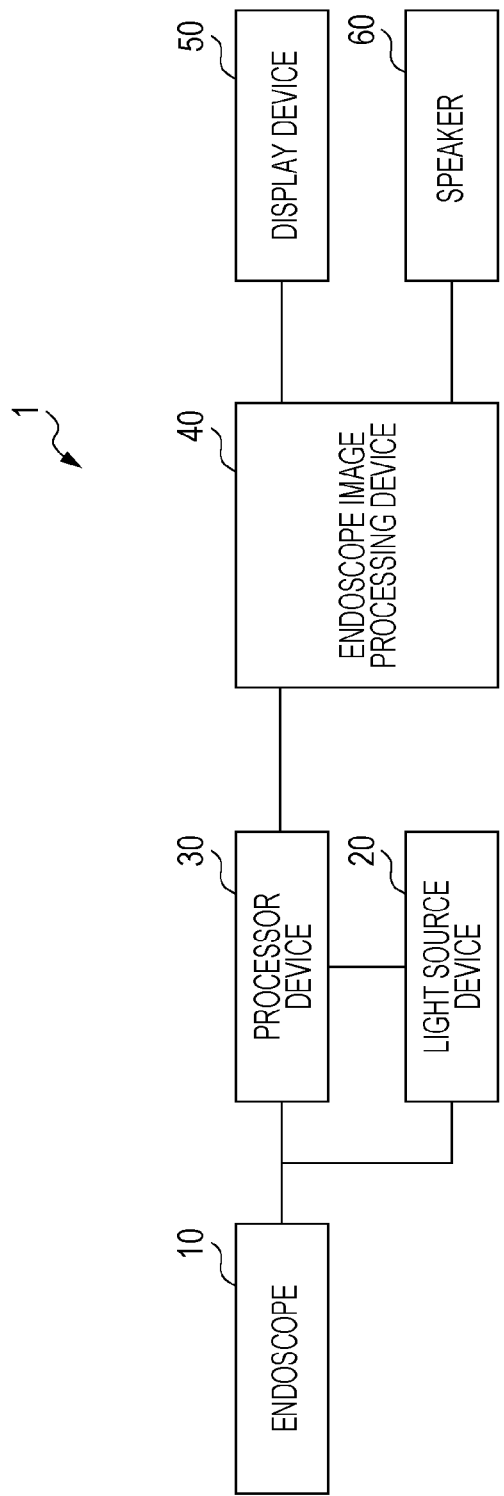
FIG. 13 is a system configuration diagram of the endoscope system according to a second embodiment.

FIG. 13 is a system configuration diagram of the endoscope system according to this embodiment.

As illustrated in FIG. 13, the endoscope system 1 according to this embodiment further includes a speaker 60, which is a difference from the endoscope system 1 according to the first embodiment described above.

Figure 14:
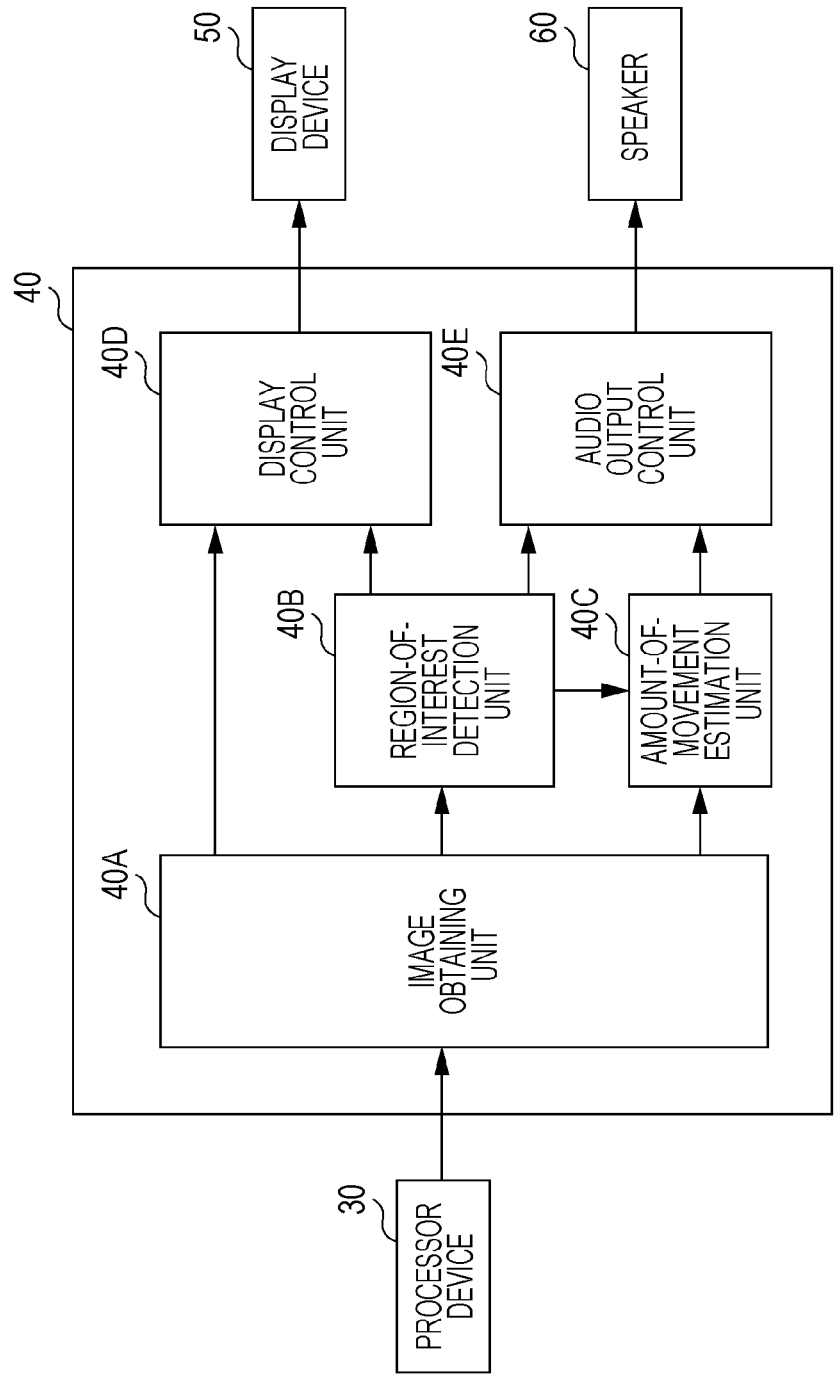
FIG. 14 is a block diagram of the functions of the endoscope image processing device in the endoscope system according to the second embodiment.

FIG. 14 is a block diagram of the functions of the endoscope image processing device.

As illustrated in FIG. 14, the endoscope image processing device 40 according to this embodiment further has a function of an audio output control unit 40E that controls output of a sound emitted from the speaker 60, which is a difference from the endoscope image processing device 40 according to the first embodiment described above. In the following description, only major differences from the endoscope image processing device 40 according to the first embodiment will be described.

In the endoscope system 1 according to this embodiment, in a case where a region of interest is detected from within an endoscopic image, the endoscopic image in which the detected region of interest X is outlined by the frame F is displayed on the display device 50 (see FIG. 5). At the same time, a predetermined notification sound (a sound for giving a notification of detection of the region of interest) is output from the speaker 60. The sound volume of the notification sound is changed in accordance with the amount of movement of the endoscope thereafter. Specifically, in a case where the amount of movement of the endoscope 10 estimated by the amount-of-movement estimation unit 40C is greater than or equal to a predetermined threshold value, the sound volume is increased.

As described above, output of the sound emitted from the speaker 60 is controlled by the audio output control unit 40E. The audio output control unit 40E controls output of the notification sound from the speaker 60 on the basis of the result of detection of a region of interest by the region-of-interest detection unit 40B and the result of estimation of the amount of movement of the endoscope by the amount-of-movement estimation unit 40C. Specifically, the following process is performed. When a region of interest is detected by the region-of-interest detection unit 40B, the audio output control unit 40E outputs the notification sound from the speaker 60 with a predetermined first sound volume. Thereafter, the audio output control unit 40E changes the sound volume of the notification sound in accordance with the amount of movement of the endoscope estimated by the amount-of-movement estimation unit 40C. Specifically, when the amount of movement becomes greater than or equal to the threshold value, the audio output control unit 40E changes the sound volume to a second sound volume louder than the first sound volume (first sound volume<second sound volume).

In the endoscope system 1 according to this embodiment, the audio output control unit 40E and the speaker 60 correspond to an example of the notification unit.

Operations

The processing procedure from detection of a region of interest to notification is the same as that in a case of giving a notification of detection by displaying the frame, and therefore, only the process after notification of detection will be described below.

In the endoscope system according to this embodiment, a notification of detection of a region of interest is given by sound, and therefore, when a region of interest is detected, a notification sound is output from the speaker 60. At this time, the notification sound is output with the first sound volume to thereby give a notification of detection of the region of interest.

Figure 15:
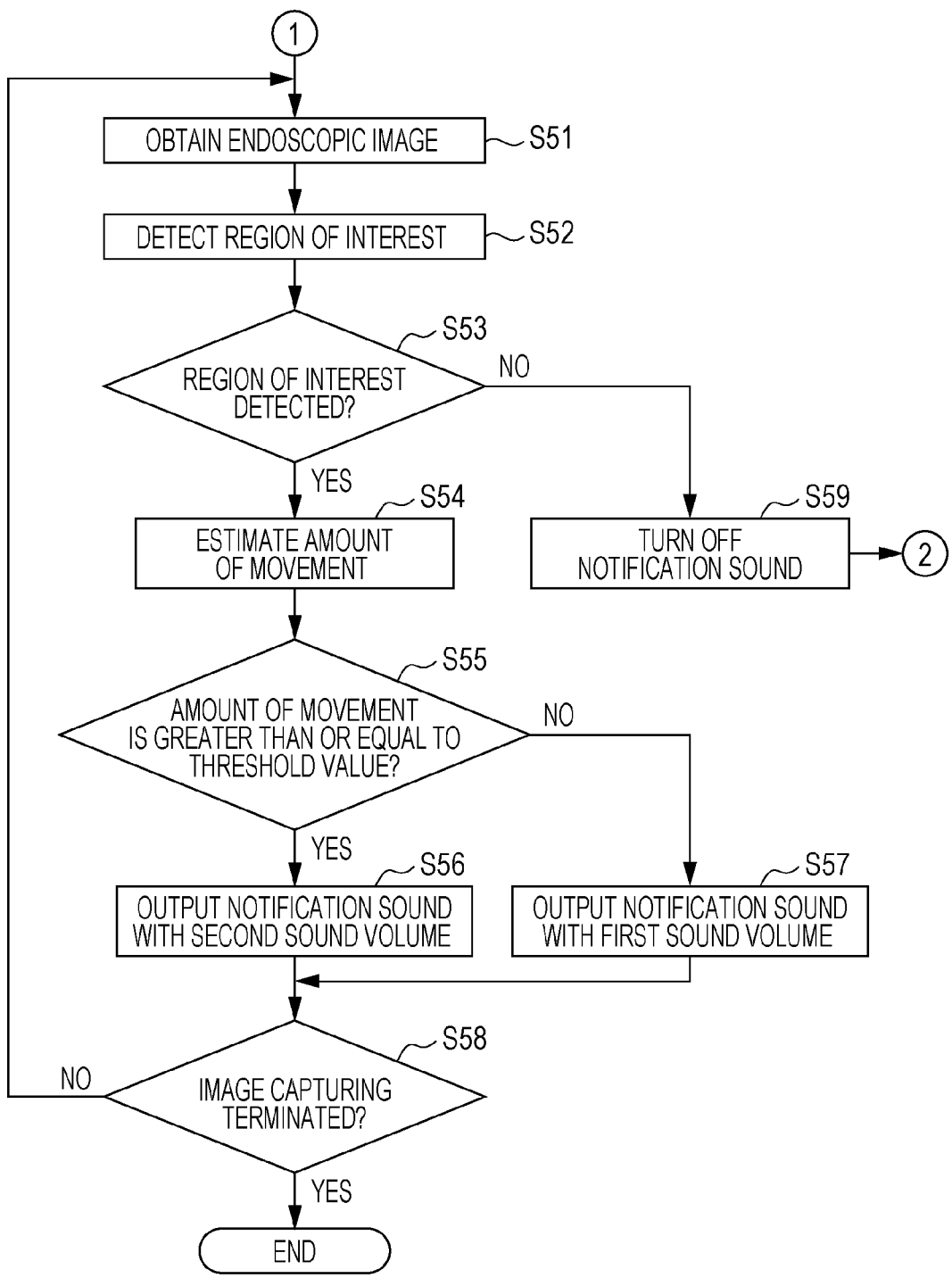
FIG. 15 is a flowchart illustrating a processing procedure after notification of detection of a region of interest.

FIG. 15 is a flowchart illustrating the processing procedure after notification of detection of a region of interest.

After notification, an endoscopic image of the next frame is first obtained (step S51). Next, detection of a region of interest is performed (step S52). Next, on the basis of the result of detection of a region of interest, it is determined whether a region of interest is detected (step S53).

In a case where no region of interest is detected (in a case of NO in step S53), output of the notification sound is turned off (step S59).

On the other hand, in a case where a region of interest is detected (in a case of YES in step S53), the amount of movement of the endoscope 10 is estimated from the image (step S54). The estimated amount of movement is compared with a threshold value, and it is determined whether the estimated amount of movement is greater than or equal to the threshold value (step S55). The threshold value is determined in advance.

In a case where the estimated amount of movement is greater than or equal to the threshold value (in a case of YES in step S55), the notification sound is output from the speaker 60 with the second sound volume that is a louder sound volume (step S56).

On the other hand, in a case where the estimated amount of movement is less than the threshold value (in a case of NO in step S55), the notification sound is output from the speaker 60 with the first sound volume (step S57).

Subsequently, it is determined whether image capturing is terminated (step S58). In a case where image capturing is terminated (in a case of YES in step S58), the process ends. In a case where image capturing is not terminated (in a case of NO in step S58), the flow returns to step S51, and the next endoscopic image is obtained.

As described above, with the endoscope system 1 according to this embodiment, a notification of detection of a region of interest is given by sound with a sound volume that is changed in accordance with the amount of movement of the endoscope 10 after detection. Accordingly, in a case where a region of interest is automatically detected, an oversight of the region of interest can be appropriately prevented.

In this embodiment, an example case where a notification of detection of a region of interest is given only by sound has been described; however, such a notification can be combined with a notification given on the screen. That is, the result of detection can be displayed by highlighting and displaying the region of interest on the display screen on which the endoscopic image is displayed, in addition to a notification by sound.

Modifications of Endoscope System according to Second Embodiment

In the above-described embodiment, a configuration is employed in which the sound volume of the notification sound is changed in accordance with the amount of movement; however, another configuration can be employed in which the tone or type of the notification sound is changed. Further, a configuration can be employed in which a combination of the sound volume, tone, and type is changed.

In the above-described embodiment, a configuration is employed in which the estimated amount of movement is compared with the threshold value and the sound volume of the notification sound is increased in a case where the estimated amount of movement is greater than or equal to the threshold value; however, the form in which the sound volume is changed is not limited to this. For example, a configuration can be employed in which the estimated amount of movement is compared with a threshold value, and the sound volume of the notification sound is decreased or the notification sound is turned off in a case where the estimated amount of movement is less than the threshold value. A configuration can be employed in which the estimated amount of movement is compared with a first threshold value and a second threshold value (second threshold value<first threshold value), and the sound volume is increased in a case where the amount of movement of the endoscope is greater than or equal to the first threshold value, and the sound volume is decreased or the notification sound is turned off in a case where the amount of movement is less than the second threshold value.

A configuration can be employed in which the sound volume of the notification sound is changed in stages in accordance with the amount of movement. The display form of the region of interest may be changed in association with the sound.

Third Embodiment

In the endoscope system according to this embodiment, in a case where a region of interest is automatically detected from a captured endoscopic image and when a region of interest is detected, an image showing the result of detection is displayed on the basis of the amount of movement of the endoscope thereafter. That is, in a case where the endoscope is moved for a predetermined amount of movement or more after detection, an image showing the result of detection is displayed.

The basic configuration of the endoscope system is the same as that of the first embodiment. The endoscope image processing device 40 has different functions. Therefore, only the functions of the endoscope image processing device 40 will be described below.

Figure 16:
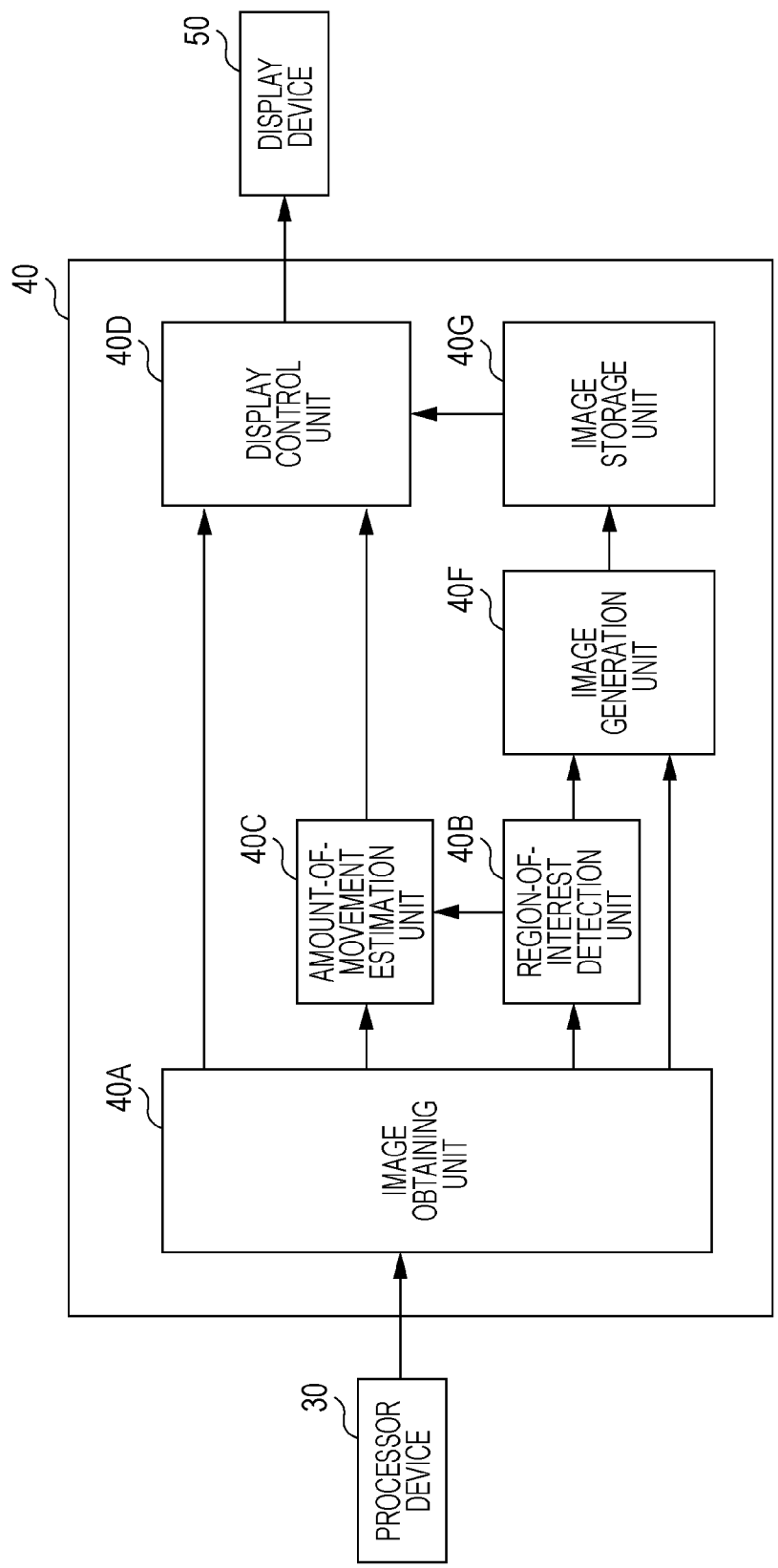
FIG. 16 is a block diagram of the functions of the endoscope image processing device in the endoscope system according to a third embodiment.

FIG. 16 is a block diagram of the functions of the endoscope image processing device according to this embodiment.

As illustrated in FIG. 16, the endoscope image processing device 40 further has functions of an image generation unit 40F that generates an image showing the result of detection of a region of interest and an image storage unit 40G that stores the image generated by the image generation unit 40F, which are differences from the endoscope image processing device 40 according to the first embodiment described above.

Figure 17:
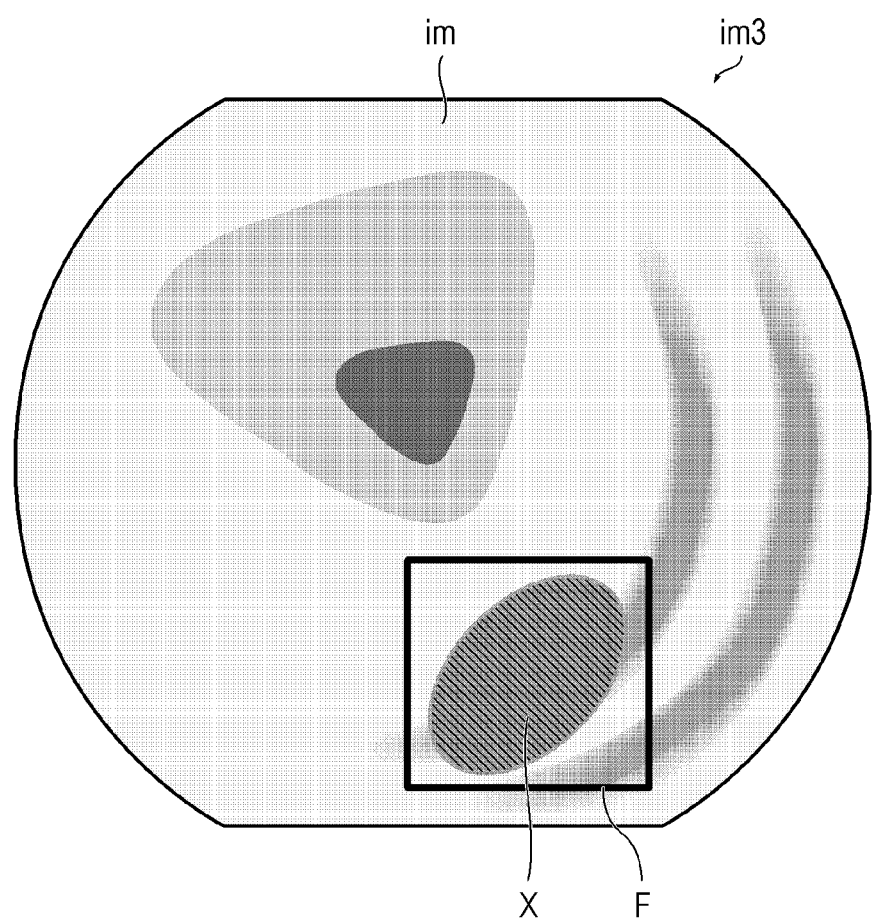
FIG. 17 is a diagram illustrating an example highlighted image.

The image generation unit 40F generates as an image showing the result of detection of a region of interest, an image (highlighted image) obtained by highlighting the region of interest in the endoscopic image. The image generation unit 40F generates a highlighted image from the endoscopic image obtained by the image obtaining unit 40A, on the basis of the result of detection of the region of interest by the region-of-interest detection unit 40B. FIG. 17 is a diagram illustrating an example highlighted image. As illustrated in FIG. 17, a highlighted image im3 is an image obtained by outlining the region of interest (the hatched elliptic region in FIG. 17) X by the rectangular frame F in an endoscopic image im. The image generation unit 40F is an example of an information generation unit. The highlighted image is an example of information indicating the result of detection of a region of interest.

The image storage unit 40G stores the highlighted image generated by the image generation unit 40F. The image generation unit 40F successively generates highlighted images and the image storage unit 40G overwrites the highlighted image stored therein with a newly generated highlighted image repeatedly. Therefore, in the image storage unit 40G, the latest highlighted image is stored. The image storage unit 40G is formed of a RAM. The image storage unit 40G is an example of a storage unit.

The display control unit 40D displays the endoscopic image obtained by the image obtaining unit 40A (the image captured by the endoscope 10) on the display device 50. At this time, the display control unit 40D displays the endoscopic image in a first display region A1 set within the screen of the display device 50. The display control unit 40D displays the highlighted image stored in the image storage unit 40G on the display device 50 under a specific condition. The condition on which the highlighted image is displayed is a condition that a region of interest is detected by the region-of-interest detection unit 40B and the amount of movement of the endoscope 10 thereafter is greater than or equal to a threshold value. The amount of movement of the endoscope 10 is the amount of movement of the endoscope 10 estimated by the amount-of-movement estimation unit 40C after detection of the region of interest. In a case where this condition is satisfied, the highlighted image is displayed on the display device 50. The highlighted image is displayed in a second display region A2 set within the screen of the display device 50. The second display region A2 is a region different from the first display region A1.

Figure 18:
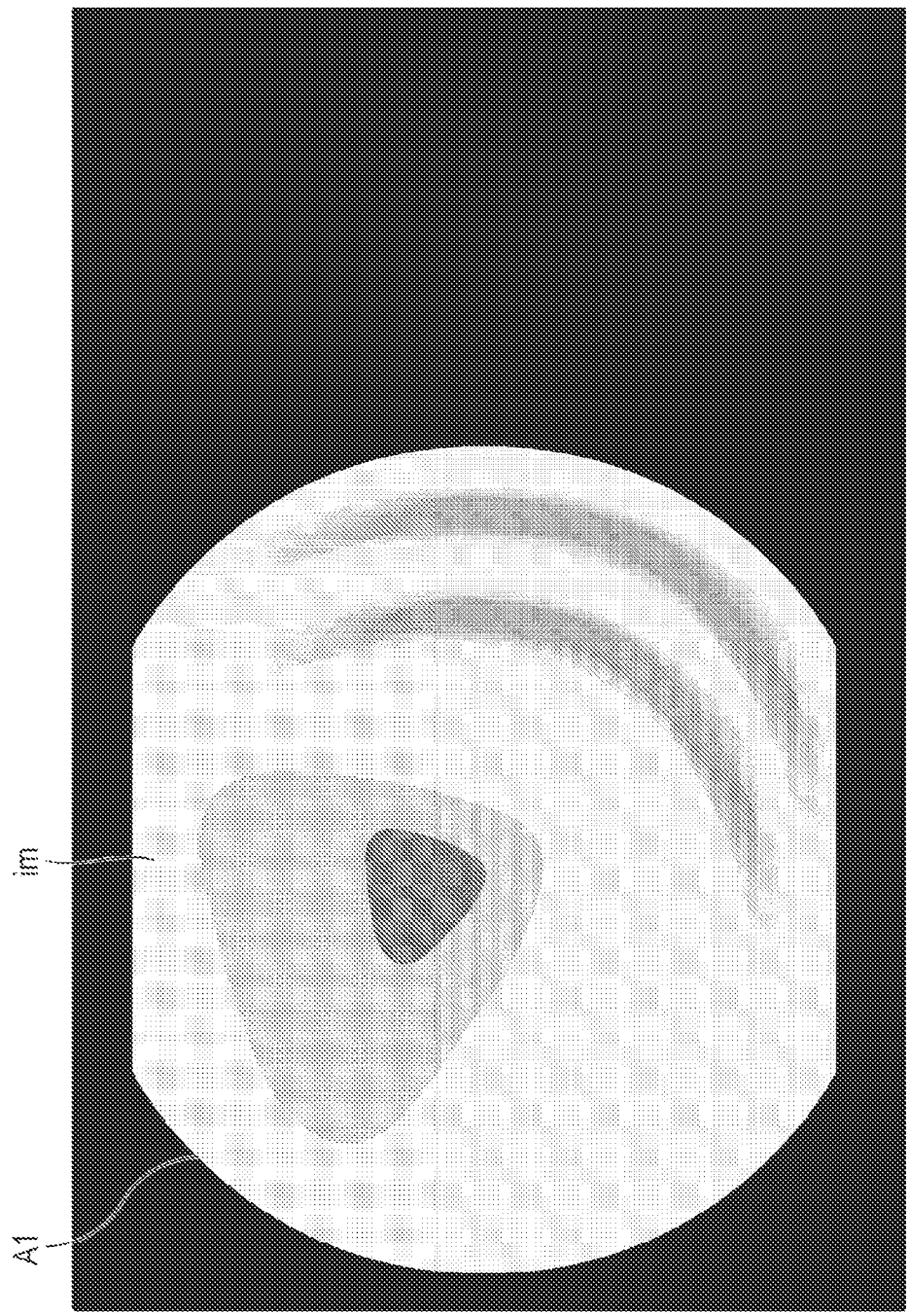
FIG. 18 is a diagram illustrating an example display image in a normal display state.

FIG. 18 is a diagram illustrating an example display image in a normal display state. Note that "normal display state" refers to a state where no highlighted image is displayed.

As illustrated in FIG. 18, in the normal display state, only the endoscopic image im captured by the endoscope 10 is displayed on the screen. The endoscopic image im is displayed in the first display region A1.

Figure 19:
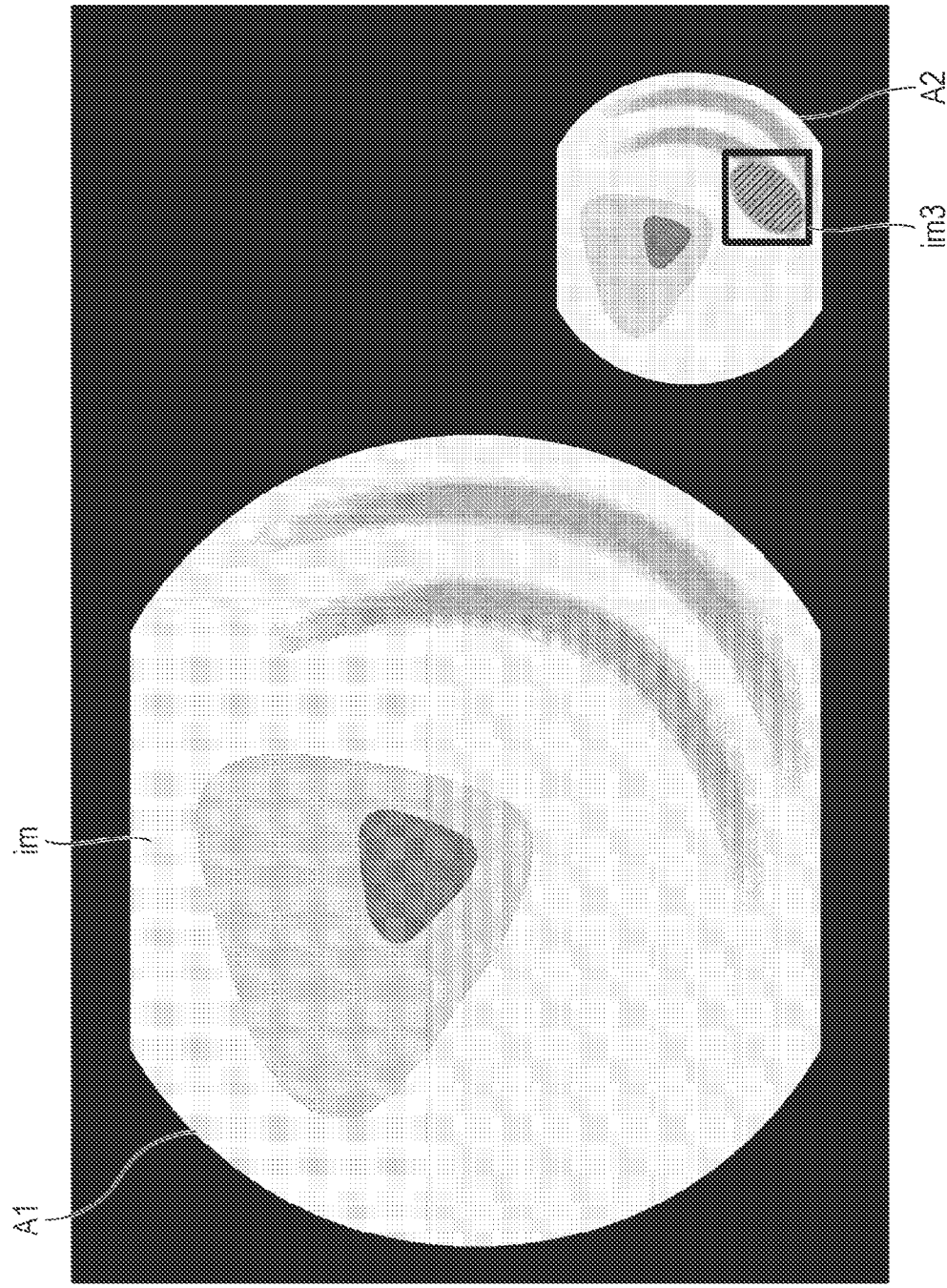
FIG. 19 is a diagram illustrating an example display image in a case where a highlighted image is displayed.

FIG. 19 is a diagram illustrating an example display image in a case where a highlighted image is displayed.

As illustrated in FIG. 19, the endoscopic image im captured by the endoscope 10 is displayed in the first display region A1 and the highlighted image im3 is displayed in the second display region A2.

In the examples illustrated in FIG. 18 and FIG. 19, the first display region A1 (main window) is set in a position to the left of the screen as a large region, and the second display region A2 (sub-window) is set in a bottom right position of the screen as a small region.

The display control unit 40D determines whether to display the highlighted image on the basis of the amount of movement of the endoscope 10 estimated by the amount-of-movement estimation unit 40C. Specifically, the amount of movement of the endoscope 10 estimated by the amount-of-movement estimation unit 40C is compared with the threshold value, and in a case where the amount of movement is greater than or equal to the threshold value, the display control unit 40D determines that the highlighted image is to be displayed in the second display region A2.

The amount-of-movement estimation unit 40C performs the estimation process for the amount of movement in a case where a region of interest is detected by the region-of-interest detection unit 40B. Therefore, only in a case where a region of interest is detected, the result of estimation of the amount of movement of the endoscope 10 thereafter is output to the display control unit 40D.

Operations

Figure 20:
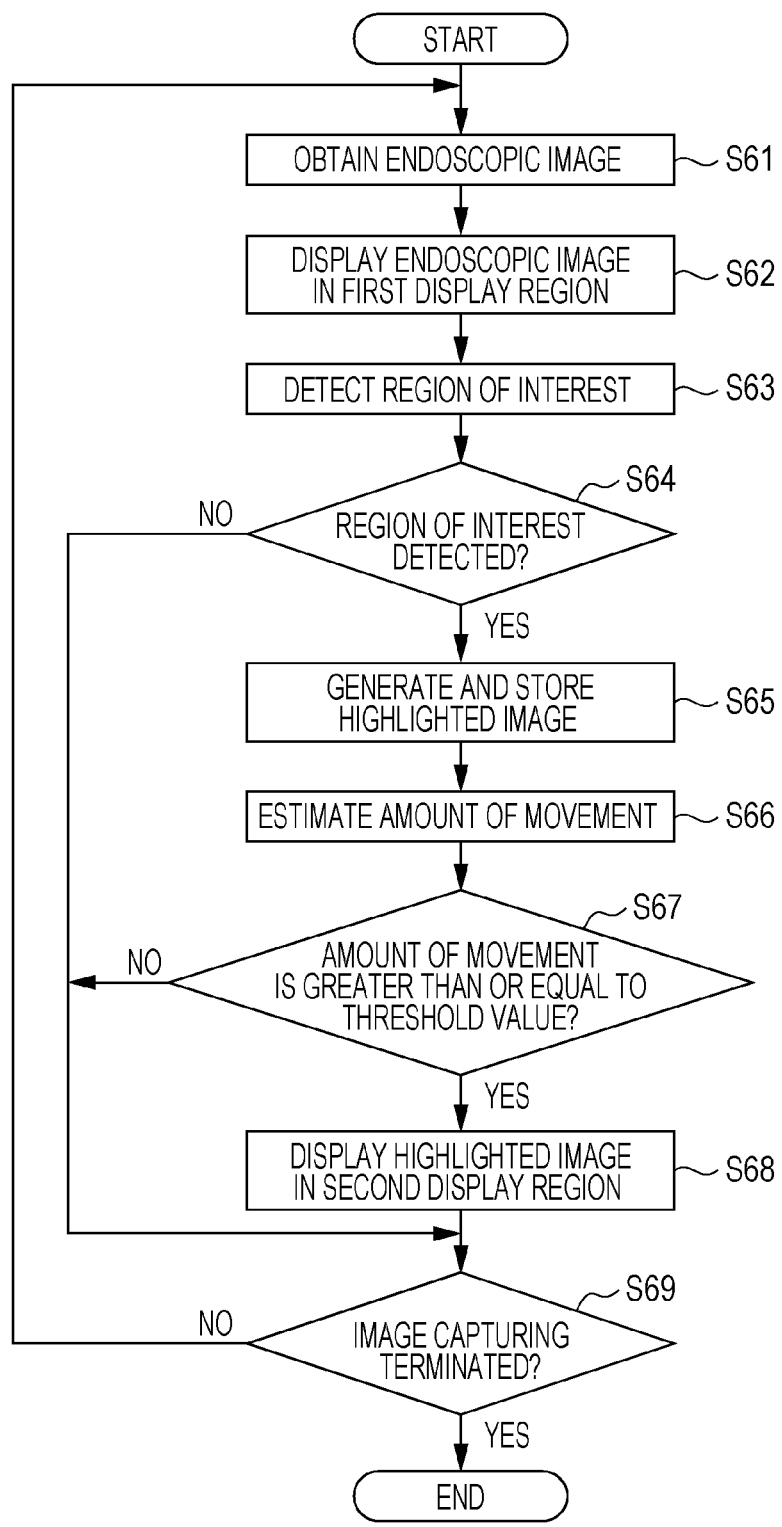
FIG. 20 is a flowchart illustrating a processing procedure for displaying an endoscopic image in the endoscope system according to the third embodiment.

FIG. 20 is a flowchart illustrating a processing procedure for displaying an endoscopic image in the endoscope system according to this embodiment.

An endoscopic image captured by the endoscope 10 is first obtained (step S61). The obtained endoscopic image is displayed on the display device 50 (step S62). The endoscopic image is displayed in the first display region A1 as illustrated in FIG. 18. Detection of a region of interest from the obtained endoscopic image is performed (step S63). On the basis of the result of detection, it is determined whether a region of interest is detected (step S64).

In a case where no region of interest is detected (in a case of NO in step S64), the flow proceeds to step S69, and it is determined whether image capturing is terminated. On the other hand, in a case where a region of interest is detected (in a case of YES in step S64), a highlighted image is generated, and the generated highlighted image is stored in the image storage unit 40G (step S65).

When a region of interest is detected, the amount of movement of the endoscope 10 is estimated from the image (step S66). The estimated amount of movement is compared with the threshold value, and it is determined whether the estimated amount of movement is greater than or equal to the threshold value (step S67).

In a case where the estimated amount of movement is less than the threshold value (in a case of NO in step S67), the flow proceeds to step S69, and it is determined whether image capturing is terminated. On the other hand, in a case where the estimated amount of movement is greater than or equal to the threshold value (in a case of YES in step S67), an image in which the highlighted image im3 is displayed in the second display region A2 is displayed on the display device 50 as illustrated in FIG. 19 (step S68). Subsequently, it is determined whether image capturing is terminated (step S69). In a case where image capturing is terminated (in a case of YES in step S69), the process ends. In a case where image capturing is not terminated (in a case of NO in step S69), the flow returns to step S61, and the next endoscopic image is obtained.

The highlighted image displayed in the second display region A2 is erased after the elapse of a specific time since the last display. The time until erasure is determined in advance (for example, 6 seconds). Note that the operator may be allowed to set the time as desired.

As described above, with the endoscope system according to this embodiment, an image showing the result of detection of a region of interest is displayed on the display device 50 only in a case where the endoscope 10 is moved for a predetermined amount of movement or more.

In a case where a region of interest is detected from a few frames, the operator who fails to notice a lesion may overlook the lesion. In this case, when an image that shows the result of detection of the region of interest is displayed on the display device 50, the possibility of an oversight can be reduced. Meanwhile, the image that is displayed even in a case where the operator notices the lesion may be redundant information and can result in a decrease in the operator's concentration.

With the endoscope system according to this embodiment, an image showing the result of detection of a region of interest is displayed on the display device 50 only in a case where the endoscope 10 is moved for a predetermined amount of movement or more, and therefore, a notification of detection can be appropriately given. That is, the result is displayed only in a case where the possibility of oversight is high, and therefore, a notification of detection can be appropriately given. The case where the possibility of oversight is high is a case where the endoscope 10 is moved to a large degree after automatic detection of the region of interest. Accordingly, the possibility of oversight can be reduced without affecting the diagnosis.

Modifications of Endoscope System according to Third Embodiment

In the above-described embodiment, a configuration is employed in which the sound volume of the notification sound is changed in accordance with the amount of movement; however, another configuration can be employed in which the tone or type of the notification sound is changed. Further, a configuration can be employed in which a combination of the sound volume, tone, and type is changed.

In the above-described embodiment, a configuration is employed in which the estimated amount of movement is compared with the threshold value and the sound volume of the notification sound is increased in a case where the estimated amount of movement is greater than or equal to the threshold value; however, the form in which the sound volume is changed is not limited to this. For example, a configuration can be employed in which the estimated amount of movement is compared with a threshold value, and the sound volume of the notification sound is decreased or the notification sound is turned off in a case where the estimated amount of movement is less than the threshold value. A configuration can be employed in which the estimated amount of movement is compared with a first threshold value and a second threshold value (second threshold value<first threshold value), and the sound volume is increased in a case where the amount of movement of the endoscope is greater than or equal to the first threshold value, and the sound volume is decreased or the notification sound is turned off in a case where the amount of movement is less than the second threshold value.

A configuration can be employed in which the sound volume of the notification sound is changed in stages in accordance with the amount of movement. The display form of the region of interest may be changed in association with the sound.

Modifications of Endoscope System according to Third Embodiment

Modification of Highlighted Image

In the above-described embodiment, an example case where an image obtained by outlining a region of interest by a frame in an endoscopic image is generated as a highlighted image has been described, however, the configuration of the highlighted image is not limited to this. Any image may be a highlighted image as long as a region of interest in the endoscopic image is identifiable.

Modification of Information indicating Result of Detection of Region of Interest In the above-described embodiment, an example case where a highlighted image is generated as information indicating the result of detection of a region of interest has been described; however, the form of information indicating the result of detection of a region of interest is not limited to this. In addition, for example, an image (cropped image) obtained by cutting a region of interest from an endoscopic image may be generated as information indicating the result of detection of the region of interest. FIG. 21 is a conceptual diagram illustrating generation of a cropped image. As illustrated in FIG. 21, an image of a region W including the region of interest X is cut from the endoscopic image im to thereby generate a cropped image im4. In a case where information indicating the result of detection of the region of interest is displayed, the cropped image im4 is displayed in the second display region A2.

Notification of Region of Interest by Sound

In a case where a region of interest is detected, a notification of the detection may be given by sound. Even in a case where notification by sound is used, the operator may fail to recognize the region of interest on the screen. In such a case, when the amount of movement after notification does not decrease, it is determined that the operator overlooks the region of interest, and the result of detection of the region of interest is displayed. Accordingly, an oversight can be appropriately prevented.

Other Embodiments

Estimation Method for Amount of Movement

In the above-described embodiments, a configuration is employed in which, to estimate the amount of movement of the endoscope (device that captures a medical image), the amount of movement of the endoscope is estimated on the basis of the amount of shift of the entire image between the two successive frames; however, the method for estimating the amount of movement of the endoscope is not limited to this. In addition, for example, the amount of movement of the endoscope can be estimated on the basis of the amount of shift of a region of interest in the endoscopic image. Regarding the amount of shift of a region of interest, for example, a set of corresponding feature points in two successive frames are extracted from the region of interest. On the basis of the positional relationship between the extracted feature points, a motion vector of the region of interest is obtained. The magnitude of the obtained motion vector is obtained as the amount of shift of the region of interest. In a case where a plurality of sets of feature points are extracted, the average of the magnitudes of motion vectors obtained from the respective sets of feature points is calculated and obtained as the amount of shift of the region of interest.

In addition, as the method for estimating the amount of movement of the endoscope (device that captures a medical image) from an endoscopic image, various publicly known methods (including a method for estimating the amount of movement of the imaging unit from time-series images (moving image)) can be employed.

Application to Other Medical Image Processing Systems

In the above-described embodiments, an example case where the present invention is applied to the system (endoscope system) that processes an image (endoscopic image) captured by the endoscope as a medical image has been described; however, application of the present invention is not limited to this. In addition, for example, the present invention is applicable to, for example, a system (ultrasonic diagnosis system) that processes an ultrasonic diagnosis image as a medical image. In an ultrasonic diagnosis system, an operation of searching for a lesion while moving an ultrasonic probe (device that captures a medical image) is performed as in the endoscope system. Therefore, the present invention is effective as in the endoscope system. The present invention is similarly applicable to a system, other than an ultrasonic diagnosis system, in which an operation of searching for a lesion and so on while moving a device is performed, and can effectively function.

Hardware Configuration of Endoscope Image Processing Device

The functions of the endoscope image processing device can be implemented as various processors. The various processors include a CPU, which is a general-purpose processor executing a program to function as various processing units, a programmable logic device (PLD), such as an FPGA (field-programmable gate array), which is a processor having a circuit configuration that is changeable after manufacture, and a dedicated electric circuit, such as an ASIC (application-specific integrated circuit), which is a processor having a circuit configuration specifically designed to perform specific processing.

One processing unit may be configured as one of the various processors or two or more processors of the same type or different types. For example, one processing unit may be configured as a plurality of FPGAs or a combination of a CPU and an FPGA. Further, a plurality of processing units may be configured as one processor. As the first example of configuring a plurality of processing units as one processor, a form is possible where one or more CPUs and software are combined to configure one processor, and the processor functions as the plurality of processing units, a representative example of which is a computer, such as a client or a server. As the second example thereof, a form is possible where a processor is used in which the functions of the entire system including the plurality of processing units are implemented as one IC (integrated circuit) chip, a representative example of which is a system on chip (SoC). As described above, regarding the hardware configuration, the various processing units are configured by using one or more of the various processors described above.

Further, the hardware configuration of the various processors is more specifically an electric circuit (circuitry) in which circuit elements, such as semiconductor elements, are combined.

The functions of the endoscope image processing device can be installed in a processor device that constitutes an endoscope apparatus.

Illumination Light

As the illumination light, light in various wavelength ranges suitable for observation, that is, white light, light in one or more specific wavelength ranges, or a combination thereof, is selected. "Specific wavelength range" is a range narrower than the wavelength range of white. Specific examples of the specific wavelength range will be described below.

A first example of the specific wavelength range is, for example, the blue range or the green range in the visible range. The wavelength range of the first example includes a wavelength range of 390 nm or more and 450 nm or less or a wavelength range of 530 nm or more and 550 nm or less, and light of the first example has its peak wavelength in a wavelength range of 390 nm or more and 450 nm or less or in a wavelength range of 530 nm or more and 550 nm or less.

A second example of the specific wavelength range is, for example, the red range in the visible range. The wavelength range of the second example includes a wavelength range of 585 nm or more and 615 nm or less or a wavelength range of 610 nm or more and 730 nm or less, and light of the second example has its peak wavelength in a wavelength range of 585 nm or more and 615 nm or less or in a wavelength range of 610 nm or more and 730 nm or less.

A third example of the specific wavelength range includes a wavelength range in which the light absorption coefficient differs between oxyhemoglobin and reduced hemoglobin, and light of the third example has its peak wavelength in a wavelength range in which the light absorption coefficient differs between oxyhemoglobin and reduced hemoglobin. The wavelength range of the third example includes a wavelength range of 400±10 nm or 440±10 nm, a wavelength range of 470±10 nm, or a wavelength range of 600 nm or more and 750 nm or less, and light of the third example has its peak wavelength in a wavelength range of 400±10 nm, 440±10 nm, 470±10 nm, or 600 nm or more and 750 nm or less described above.

A fourth example of the specific wavelength range is the wavelength range of excitation light that is used in observation (fluorescence observation) of fluorescence emitted from a fluorescent substance in the living body and that excites the fluorescent substance, and is a wavelength range of, for example, 390 nm to 470 nm.

A fifth example of the specific wavelength range is the wavelength range of infrared light. The wavelength range of the fifth example includes a wavelength range of 790 nm or more and 820 nm or less or a wavelength range of 905 nm or more and 970 nm or less, and light of the fifth example has its peak wavelength in a wavelength range of 790 nm or more and 820 nm or less or in a wavelength range of 905 nm or more and 970 nm or less.

Switching of Illumination Light

As the type of the light source, a laser light source, a xenon light source, an LED light source (LED: light-emitting diode), or a combination of any of these light sources can be employed as appropriate. It is preferable to configure the type and wavelength of the light source, the presence or absence of a filter, and so on in accordance with, for example, the type of photographic subject or the purpose of observation. During observation, it is preferable to combine wavelengths of the illumination light and/or switch the wavelength of the illumination light in accordance with, for example, the type of photographic subject or the purpose of observation. In a case where the wavelength is switched, for example, a disc-shaped filter (rotary color filter) that is disposed in front of the light source and includes a filter for transmitting or blocking light having a specific wavelength may be rotated to thereby switch the wavelength of light for irradiation.

Imaging Unit

The image sensor included in the imaging unit of the endoscope is not limited to a color image sensor in which color filters are disposed for respective pixels and may be a monochrome image sensor. In a case where a monochrome image sensor is used, the wavelength of illumination light is sequentially switched to other wavelengths to capture images in a planar-sequential manner or a color-sequential manner. For example, the wavelength of emitted illumination light may be sequentially switched to violet, blue, green, and red, or white light may be emitted and the wavelength of emitted illumination light may be switched by a rotary color filter (for example, red, green, and blue). One or more narrow-band light rays may be emitted, and the wavelength of emitted illumination light may be switched by a rotary color filter. The narrow-band light rays may be infrared rays having two or more different wavelengths.

Example Generation of Special-Light Image

The processor device may generate an image (special-light image) having information about a specific wavelength range on the basis of an image (normal-light image) obtained by image capturing using white light. The processor device can obtain a signal of a specific wavelength range by performing calculation based on color information of red (R), green (G), and blue (B) or cyan (C), magenta (M), and yellow (Y) included in a normal-light image.

Program for Causing Computer to Implement Functions of Endoscope Image Processing Device A program for causing a computer to implement the functions of the endoscope image processing device described in the above-described embodiments can be recorded to a computer-readable medium that is a tangible non-transitory information storage medium, such as an optical disc, a magnetic disc, or a semiconductor memory, and provided via the information storage medium. Instead of the form in which the program is stored in the tangible non-transitory information storage medium and provided, a program signal can be provided as a download service by using a telecommunication line, such as the Internet.

Some or all of the functions of the endoscope image processing device described in the above-described embodiments can be provided as an application server to provide a service that provides processing functions via a telecommunication line.

Combination of Embodiments, Modifications, and so on

Constituent elements described in the above-described embodiments and constituent elements described in the modifications can be combined as appropriate, or some of the constituent elements can be replaced.

REFERENCE SIGNS LIST 1 endoscope system
10 endoscope
12 insertion part
12A tip part
12B bending part
12C soft part
12a imaging unit
14 operation part
14A angle knob
14B air/water supply button
14C suction button
14D shutter button
16 connection part
16A connector
16B connector
20 light source device
30 processor device
40 endoscope image processing device
40A image obtaining unit
40B region-of-interest detection unit
40C amount-of-movement estimation unit
40D display control unit
40E audio output control unit
40F image generation unit
40G image storage unit
50 display device
60 speaker
A display region
A1 first display region
A2 second display region
F frame
W region from which cropped image is cut X region of interest
im endoscopic image
im1 endoscopic image
im2 endoscopic image
im3 highlighted image
im4 cropped image
S1 to S5 processing procedure from detection of region of interest to notification
S11 to S19 processing procedure after notification of detection of region of interest
S21 to S29 processing procedure after notification of detection of region of interest
S31 to S41 processing procedure after notification of detection of region of interest
S51 to S59 processing procedure after notification of detection of region of interest
S61 to S69 processing procedure for display of endoscopic image

What is claimed is:

1. A medical image processing system comprising one or more processors configured to:
obtain a medical image;
display the medical image on a monitor;
detect a region of interest from within the medical image;
estimate an amount of movement of a device that captures the medical image, on the basis of the medical image;
highlight the region of interest in the medical image displayed on the monitor to give a notification of detection of the region of interest in a case where the region of interest is detected; and
increase a degree of highlight of the region of interest in a case where the estimated amount of movement after the notification of the region of interest is greater than or equal to a threshold value.

2. The medical image processing system according to claim 1, wherein the one or more processors are configured to estimate the amount of movement in the case where the region of interest is detected.

3. The medical image processing system according to claim 1, wherein the one or more processors are configured to highlight the region of interest by outlining the region of interest by a frame in the medical image displayed on the monitor.

4. The medical image processing system according to claim 3, wherein the one or more processors are configured to change the degree of highlight of the region of interest by changing at least one of a thickness, a line type, a color, a shape, a degree of blinking, or a brightness of the frame.

5. A medical image processing system comprising one or more processors configured to:
obtain a medical image;
display the medical image on a monitor;
detect a region of interest from within the medical image;
estimate an amount of movement of a device that captures the medical image, on the basis of the medical image;
highlight the region of interest in the medical image displayed on the monitor to give a notification of detection of the region of interest in a case where the region of interest is detected; and
decrease a degree of highlight of the region of interest or turn off highlighting of the region of interest in a case where the estimated amount of movement after the notification of the region of interest is less than a threshold value.

6. The medical image processing system according to claim 1, wherein
the one or more processors are configured to decrease the degree of highlight of the region of interest or turn off highlighting of the region of interest in a case where the estimated amount of movement after the notification of the region of interest is less than another threshold value.

7. A medical image processing system comprising one or more processors configured to:
obtain a medical image;
display the medical image on a monitor;
detect a region of interest from within the medical image;
estimate an amount of movement of a device that captures the medical image, on the basis of the medical image;
cause a speaker to emit a sound to give a notification of detection of the region of interest in a case where the region of interest is detected; and
increase a sound volume of the sound in a case where the estimated amount of movement after the notification of the region of interest is greater than or equal to a threshold value.

8. A medical image processing system comprising one or more processors configured to:
obtain a medical image;
detect a region of interest from within the medical image;
generate information indicating a result of detection in a case where the region of interest is detected;
store the generated information in a storage;
in a case where the region of interest is detected, estimate an amount of movement of a device that captures the medical image, on the basis of the medical image;
display the medical image in a first display region of a monitor having the first display region and a second display region within a screen; and
in a case where the region of interest is detected and where the estimated amount of movement after the detection of the region of interest is greater than or equal to a threshold value, display the information stored in the storage in the second display region.

9. The medical image processing system according to claim 8, wherein the one or more processors are configured to generate as the information indicating the result of detection of the region of interest, an image obtained by highlighting the region of interest in the medical image.

10. The medical image processing system according to claim 9, wherein the one or more processors are configured to generate an image obtained by highlighting the region of interest by outlining the region of interest by a frame in the medical image.

11. The medical image processing system according to claim 8, wherein the one or more processors are configured to generate as the information indicating the result of detection of the region of interest, an image obtained by cutting the region of interest from the medical image.

12. The medical image processing system according to claim 1, wherein the one or more processors are configured to estimate the amount of movement at predetermined frame intervals.

13. The medical image processing system according to claim 12, wherein the one or more processors are configured to estimate the amount of movement on the basis of an amount of shift of an entire medical image.

14. The medical image processing system according to claim 12, wherein the one or more processors are configured to estimate the amount of movement on the basis of an amount of shift of the region of interest.

15. A medical image processing system comprising one or more processors configured to:

obtain a medical image;
display the medical image on a monitor;
detect a region of interest from within the medical image;
estimate an amount of movement of a device that captures the medical image, on the basis of the medical image;
cause a speaker to emit a sound to give a notification of detection of the region of interest in a case where the region of interest is detected; and
decrease a sound volume of the sound or turn off the sound in a case where the estimated amount of movement after the notification of the region of interest is less than a threshold value.

16. The medical image processing system according to claim 7, wherein the one or more processers are configured to decrease the sound volume of the sound or turn off the sound in a case where the estimated amount of movement after the notification of the region of interest is less than another threshold value.

* * * * *